US012786644B2

(12) United States Patent
Kim et al.

(10) Patent No.: US 12,786,644 B2
(45) Date of Patent: Nov. 3, 2026

(54) TINNITUS TREATMENT DEVICE AND SYSTEM USING SURROUND SOUND VIRTUAL REALITY INTERFACE, AND OPERATION METHOD THEREOF

(71) Applicants: INDUSTRY-UNIVERSITY COOPERATION FOUNDATION HANYANG UNIVERSITY ERICA CAMPUS, Ansan-si (KR); KOREA UNIVERSITY RESEARCH AND BUSINESS FOUNDATION, Seoul (KR)

(72) Inventors: Kibum Kim, Ansan-si Gyeonggi-do (KR); June Choi, Ansan-si (KR); Sangsun Han, Ansan-si Gyeonggi-do (KR); Hojun Aan, Changwon-si (KR); Edgar felipe Canasto Jimenez, Ansan-si Gyeonggi-do (KR); Dongheun Park, Seoul (KR); Jeonghwan Kim, Seoul (KR); Intae Hwang, Seoul (KR)

(73) Assignees: INDUSTRY-UNIVERSITY COOPERATION FOUNDATION HANYANG UNIVERSITY ERICA CAMPUS, Ansan-si (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 195 days.

(21) Appl. No.: 18/723,330

(22) PCT Filed: Nov. 30, 2022

(86) PCT No.: PCT/KR2022/019137
§ 371 (c)(1),
(2) Date: Jun. 21, 2024

(87) PCT Pub. No.: WO2023/121031
PCT Pub. Date: Jun. 29, 2023

(65) Prior Publication Data

US 2025/0373993 A1 Dec. 4, 2025

(30) Foreign Application Priority Data

Dec. 21, 2021 (KR) ........................ 10-2021-0183392
Sep. 29, 2022 (KR) ........................ 10-2022-0124459
Nov. 22, 2022 (KR) ........................ 10-2022-0156867

(51) Int. Cl.
*H04R 25/00* (2006.01)
*A61B 5/00* (2006.01)
(Continued)

(52) U.S. Cl.
CPC ............. *H04R 25/75* (2013.01); *A61B 5/128* (2013.01); *A61F 11/04* (2013.01); *A61M 21/00* (2013.01);
(Continued)

(58) Field of Classification Search
CPC ......... H04R 25/75; A61B 5/128; A61F 11/04; A61M 21/00; A61M 2021/0027; G06F 3/011
See application file for complete search history.

(56) References Cited

U.S. PATENT DOCUMENTS 9,992,590 B2 6/2018 Baker
2014/0257131 A1 9/2014 Polley et al.
(Continued)

FOREIGN PATENT DOCUMENTS

KR 10-1802995 B1 11/2017
KR 10-2080591 B1 2/2020
(Continued)

OTHER PUBLICATIONS

Londero et al., "Auditory and Visual 3D virtual Reality Therapy for Chronic Subjective Tinnitus: Theoretical Framework," Sep. 25, 2009, pp. 143-151 (Year: 2009).*
(Continued)

*Primary Examiner* — Mallika D Fairchild
*Assistant Examiner* — Thien Jason Tran

(57) ABSTRACT

A tinnitus treatment device using a surround sound virtual reality (VR) interface of the present invention includes a display unit that is mounted on a user's head to display a VR video, into which a tinnitus avatar is inserted, to a subject, a virtual environment object unit that generates the tinnitus avatar by visualizing the tinnitus perceived by the user, a surround sound processing unit that generates a 3D sound so as to allow the user to perceive a mixed sound combined with the tinnitus, a sound output unit that outputs the 3D sound to the user, and a VR video control unit that changes content in the VR video in response to a user input signal provided from a user interface, in which the VR video control unit controls the tinnitus avatar displayed in the VR video in response to the user input signal and changes the output of the 3D sound in response to the control of the tinnitus avatar.

14 Claims, 14 Drawing Sheets

(51) Int. Cl.

| | |
|---|---|
| ***A61B 5/12*** | (2006.01) |
| ***A61F 11/00*** | (2022.01) |
| ***A61F 11/04*** | (2006.01) |
| ***A61M 21/00*** | (2006.01) |
| ***G06F 3/01*** | (2006.01) |

(52) U.S. Cl.
CPC ..... *G06F 3/011* (2013.01); *A61M 2021/0027* (2013.01); *A61M 2021/005* (2013.01); *A61M 2205/507* (2013.01)

(56) References Cited

U.S. PATENT DOCUMENTS

| | | | |
|---|---|---|---|
| 2017/0042739 A1 | 2/2017 | O'Neill et al. | |
| 2018/0126115 A1 | 5/2018 | Searchfield et al. | |
| 2018/0271710 A1* | 9/2018 | Boesen ................ | A61B 5/7203 |
| 2021/0338969 A1 | 11/2021 | Snow | |

FOREIGN PATENT DOCUMENTS

| | | |
|---|---|---|
| KR | 10-2021-0036021 A | 4/2021 |
| WO | 2020/128053 A3 | 6/2020 |

OTHER PUBLICATIONS

International Search Report issued from the WIPO dated Mar. 17, 2023 for the PCT International Application No. PCT/KR2022/019137.

Written Opinion of International Search Authority issued from the WIPO dated Mar. 17, 2023 for the PCT International Application No. PCT/KR2022/019137.

Londero, Alain et al. Auditory and visual 3D virtual reality therapy for chronic subjective tinnitus: theoretical framework. Virtual Reality. 14, pp. 143-151, Sep. 25, 2009.

Wolf, Dennis et al. Face/On: Multi-Modal Haptic Feedback for Head-Mounted Displays in Virtual Reality. IEEE Transactions on Visualization and Computer Graphics. vol. 25, Issue 11, pp. 3169-3177, Aug. 12, 2019.

Snoswell, Aaron J. et al. Immersive Virtual Reality in Health Care: Systematic Review of Technology and Disease States. JMIR Biomedical Engineering. vol. 4, Issue 1, el5025, pp. 1-16, Sep. 26, 2019.

Park, Dong Heun et al. A clinical trial of a patient-customized virtual reality intervention for tinnitus. Scientific Reports. 12, Article No. 12441, pp. 1-11, Jul. 20, 2022.

* cited by examiner

TINNITUS TREATMENT DEVICE AND SYSTEM USING SURROUND SOUND VIRTUAL REALITY INTERFACE, AND OPERATION METHOD THEREOF

CROSS-REFERENCE TO RELATED APPLICATIONS

This application is a National Stage Entry of PCT International Application No. PCT/KR2022/019137, which was filed on Nov. 30, 2022, and which claims priority from and the benefit of Korean Patent Application No. 10-2021-0183392, filed with the Korean Intellectual Property Office on Dec. 21, 2021, Korean Patent Application No. 10-2022-0124459, filed with the Korean Intellectual Property Office on Sep. 29, 2022, and Korean Patent Application No. 10-2022-0156867, filed with the Korean Intellectual Property Office on Nov. 22, 2022. The disclosure of the above patent applications is hereby incorporated by reference in its entirety.

STATEMENT REGARDING PRIOR DISCLOSURES BY THE INVENTOR OR A JOINT INVENTOR

At least one inventor or joint inventor of the present disclosure has made related disclosures in the scientific reports (www.nature.com) on Jul. 20, 2022.

BACKGROUND

1. Technical Field

The present invention relates to a tinnitus treatment device and system using a surround sound virtual reality interface and an operation method thereof, and more particularly, to a tinnitus treatment device and system using a cognitive behavioral therapy method and an operation method thereof.

2. Related Art

Tinnitus refers to a phenomenon of hearing sound in ears or head even if there is no external sound stimulus. Tinnitus may be divided into those (auditory sensation) that occur in auditory organs themselves and those (non-auditory sensation) that are felt through the auditory organs by structures such as muscles, blood vessels, or the like surrounding the auditory organs, and auditory tinnitus is most commonly caused by damage to the auditory organs.

The conventional general tinnitus treatment method is a sound therapy method. The sound therapy method is used to modify patients' perception or response to the tinnitus by shielding a tinnitus sound using external noise. The sound therapy method may be divided into complete shielding, in which the entire tinnitus sound is shielded by a stimulating sound, and partial shielding, in which the stimulating sound partially covers the tinnitus sound.

Sound therapy is a method of allowing a patient to listen to separate stimulating sounds, but has the inconvenience of requiring a significant amount of time per day. In addition, the conventional tinnitus treatment method mainly focuses on treatment sounds, but has the problem that it is not easy to focus on the sound even in daily life.

Meanwhile, the tinnitus may be considered as a type of virtual reality which a brain perceives as important information even though it is incomplete information. The virtual reality is a technology that acquires information by stimulating the human brain so that the virtual reality is accepted as real even though it is not real. Tinnitus is also a phenomenon in which the human brain is perceived as if there is a sound stimulus even though there is no external sound stimulus, and therefore, may be considered as a type of phantom pain that allows a person to perceive virtual information.

Accordingly, as one of the tinnitus treatment methods, research is required on tinnitus retraining treatment through habituation in an area where tinnitus should be detected and habituation of response to pain due to tinnitus.

SUMMARY

Technical Problem

The present invention provides a tinnitus treatment device and system using a surround sound virtual reality interface capable of providing tinnitus retraining treatment through habituation of responses to tinnitus, and an operation method thereof.

Technical Solution

According to an embodiment, a tinnitus treatment device using a surround sound virtual reality (VR) interface includes: a display unit that is mounted on a user's head to display a VR video, into which a virtual tinnitus object and a virtual environment object are inserted, to a subject; a virtual tinnitus object and virtual environment object unit that visualizes subjective tinnitus perceived by the user to generate the virtual tinnitus object and generate the virtual environment object corresponding to a sound source occurring in the virtual environment; a surround sound processing unit that performs three-dimensional (3D) sound processing to allow the user to perceive a location of the virtual tinnitus object and a location of the virtual environment object; a sound output unit that outputs the 3D sound to the user; and a VR video control unit that changes content in the VR video in response to a user input signal provided from a user interface, in which the VR video control unit may control the virtual tinnitus object displayed in the VR video in response to the user input signal and change the output of the 3D sound in response to the control of the virtual tinnitus object.

The VR video control unit may remove the virtual tinnitus object displayed in the VR video in response to the user input signal, and at the same time stop the output of the 3D sound due to the virtual tinnitus object.

The VR video control unit may remove the virtual tinnitus object displayed in the VR video in response to the user input signal, and at the same time maintain the output of the 3D sound due to the virtual environment object while stopping the output of the 3D sound due to the virtual tinnitus object.

The VR video control unit may gradually remove the virtual tinnitus object displayed in the VR video in response to the user input signal, and at the same time gradually reduce the output of the 3D sound due to the virtual tinnitus object.

The 3D sound may be a mixed sound in which the 3D sound due to the virtual tinnitus object and the 3D sound due to the virtual environment object are mixed.

The sound output unit may include a left sound output unit and a right sound output unit that output sound to both ears of the user.

The surround sound processing unit may adjust a time, a volume, and a pitch of the 3D sound depending on a distance between the user and the virtual tinnitus object and a distance between the user and the virtual environment object within the VR video.

The surround sound processing unit may be implemented based on a head-related transfer function (HRTF) which is a function that sets a time, a volume, and a pitch of the sound according to movement of the head.

The display unit may be provided as a head mounted display (HMD) that provides a closed viewing environment blocked from an outside.

According to another embodiment, a tinnitus treatment system using a surround sound virtual reality interface includes: a tinnitus treatment device; and a VR video controller that is connected to the tinnitus treatment device through a network and inputs a user input signal to the tinnitus treatment device, in which the tinnitus treatment device may include: a display unit that is mounted on a user's head to display a VR video, into which a virtual tinnitus object and a virtual environment object are inserted, to a subject; a virtual tinnitus object and virtual environment object unit that visualizes subjective tinnitus perceived by the user to generate the virtual tinnitus object and generate the virtual environment object corresponding to a sound source occurring in the virtual environment; a surround sound processing unit that performs three-dimensional (3D) sound processing to allow the user to perceive a location of the virtual tinnitus object and a location of the virtual environment object; a sound output unit that outputs the 3D sound to the user; and a VR video control unit that changes content in the VR video in response to a user input signal provided from the VR video controller, and the VR video control unit may control the virtual tinnitus object displayed in the VR video in response to the user input signal and change the output of the 3D sound in response to the control of the virtual tinnitus object.

According to still another embodiment, a tinnitus treatment device using a surround sound virtual reality interface includes: a user interface that acquires subjective tinnitus information from a user; a processor that visualizes subjective tinnitus perceived by the user from the acquired subjective tinnitus information to generate a virtual tinnitus object and generate a virtual environment object corresponding to a sound source occurring in the virtual environment, and performs 3D sound processing to allow the user to perceive a location of the virtual tinnitus object and a location of the virtual environment object; an HMD that displays a VR video into which the virtual tinnitus object and the virtual environment object are inserted and outputs the 3D sound to a subject; and a haptic device that receives a user input signal for changing content in the VR video and transfers a corresponding tactile sensation to the user according to a change in the content in the VR video, in which the processor may control the virtual tinnitus object displayed in the VR video in response to the user input signal and change the output of the 3D sound in response to the control of the virtual tinnitus object.

The processor may gradually remove the virtual tinnitus object displayed in the VR video in response to the user input signal, and at the same time gradually reduce the output of the 3D sound due to the virtual tinnitus object.

The processor may gradually remove a size of the virtual tinnitus object displayed in the VR video in response to the user input signal, and at the same time gradually reduce the output of the 3D sound due to the virtual tinnitus object.

A level at which the size of the virtual tinnitus object is gradually reduced and a level at which the output of the 3D sound due to the virtual tinnitus object is gradually reduced may correspond to each other.

The haptic device may generate the corresponding tactile sensation when the size of the virtual tinnitus object is gradually reduced and transfer the generated tactile sensation to the user.

The haptic device may be a phantom haptic device.

BRIEF DESCRIPTION OF DRAWINGS

FIG. 8 is a diagram illustrating tinnitus treatment experimental setting according to an embodiment.

DESCRIPTION OF EXAMPLE EMBODIMENTS

Figure 1:
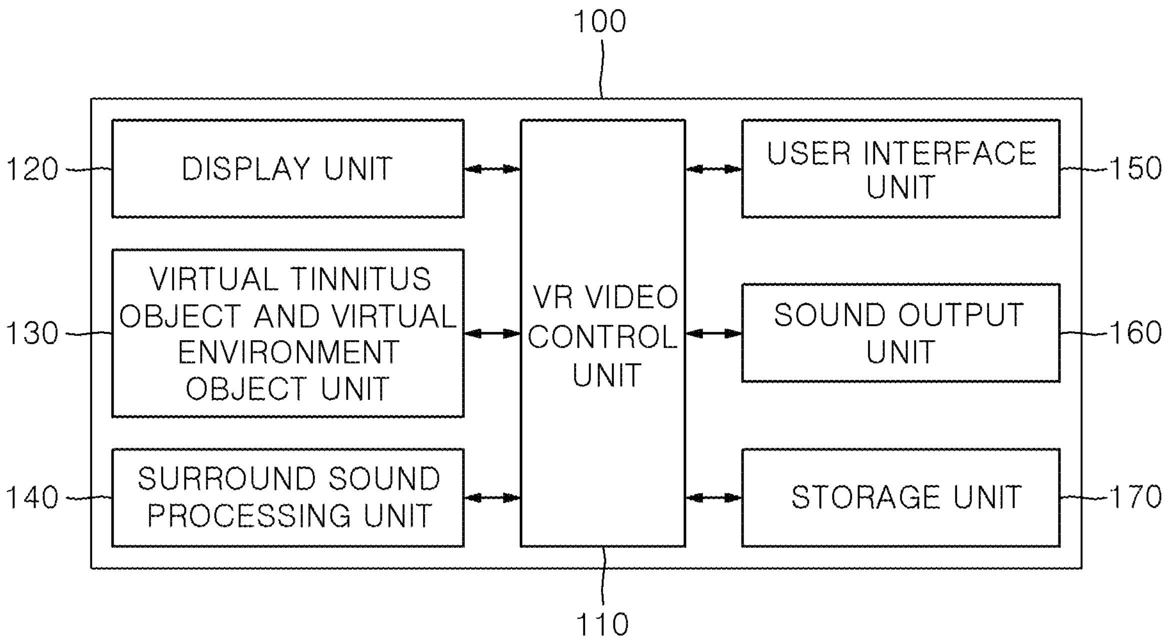
FIG. 1 is a schematic block diagram of a tinnitus treatment device using a surround sound virtual reality interface according to an embodiment.

Hereinafter, the most exemplary embodiments of the present invention are described. In the accompanying drawings, the thickness and interval are expressed for convenience of explanation and may be exaggerated compared to the actual physical thickness. In describing the present invention, well-known configurations irrelevant to the gist of the present invention may be omitted. In adding reference numerals to components throughout the drawings, it is to be noted that like reference numerals designate like components even though components are shown in different drawings.

Specific structural or functional descriptions disclosed in the present specification will be provided only in order to describe exemplary embodiments of the present invention. Therefore, exemplary embodiments of the present invention may be implemented in various forms, and the present invention is not to be interpreted as being limited to exemplary embodiments described in the present specification. In embodiments described in the present specification, a “module” or a “unit” may mean a functional unit performing at least one function or operation, and be implemented by hardware or software or be implemented by a combination of hardware and software.

Further, the term “unit” or “module” used herein means a software component or a hardware component such as a field programmable gate array (FPGA) or an application-specific integrated circuit (ASIC) and performs predetermined functions. However, the term “unit” or “module” is not meant to be limited to software or hardware. The “unit” or “module” may be stored in a storage medium that can be addressed or may be configured to regenerate one or more processors. Accordingly, for example, the “unit” or “module” includes components such as software components, object-oriented software components, class components, and task components, processors, functions, attributes, procedures, subroutines, segments of a program code, drivers, firmware, a microcode, a circuit, data, a database, data structures, tables, arrays, and variables. Functions provided in components, “units,” or “modules” may be combined into fewer components, “units,” or “modules” or further separated into additional components, “units,” or “modules.”

FIG. 1 is a schematic block diagram of a tinnitus treatment device using a surround sound virtual reality interface according to an embodiment.

Referring to FIG. 1, a tinnitus treatment device 100 using a surround sound virtual reality (VR) interface (hereinafter, simply referred to as “tinnitus treatment device”) according to the embodiment uses a VR video and 3D sound as part of brain nerve activity to provide tinnitus treatment training through a user’s active participation.

The tinnitus is a subjective sensation of noise perceived even when there is no external auditory stimulation. Pathophysiological mechanism for the subjective tinnitus is related to hyperactivation and functional reallocation of auditory and non-auditory cortical or subcortical networks. The subjective tinnitus may be accompanied not only by functional abnormalities in one part of a brain, but also by disturbances in a brain network connection, and hearing originates from the brain.

Therefore, it is necessary to monitor of brain neural activity to elucidate auditory control mechanism, and analyzing neural behavior at a cortical level, particularly a change in auditory pathway, will help improve our understanding of neural motivation and reorganization involved in the generation and maintenance of tinnitus.

For this purpose, the tinnitus treatment device 100 includes a VR video control unit 110, a display unit 120, a virtual tinnitus object and virtual environment object unit 130, a surround sound processing unit 140, a user interface unit 150, a sound output unit 160, and a storage unit 170.

The VR video control unit 110 may control a display of a VR video displayed on the display unit 120, control the output of the 3D sound output from the sound output unit 160, and determine the user’s gaze according to the user’s movement, and may insert or remove the virtual tinnitus object and the tinnitus avatar generated by the virtual environment object part into or from the VR video.

The tinnitus treatment method according to the present invention is to remove or alleviate the tinnitus symptom by the user’s active participation. The VR video control unit 110 may change content within the VR video in response to the user input signal provided from the user interface unit 150, and change the output of 3D sound in response to the change in content within the VR video.

The display unit 120 includes a plurality of pixels and may display the VR video using the input image data. For example, the display unit 120 may be implemented as an organic light emitting display panel, a liquid crystal display panel, a plasma display panel, etc., but is not limited thereto.

In addition, the display unit 120 may be provided as a head mounted display (HMD) that provides a closed viewing environment blocked from the outside. In other words, the tinnitus treatment device 100 is the HMD device that may be mounted on the user’s head to display the VR video. Since the tinnitus treatment device 100 is worn on the user’s head, the tinnitus treatment device 100 may detect a change in location of the HMD device according to the movement of the head to determine the change in the user’s gaze.

The virtual tinnitus object and virtual environment object unit 130 may visualize the tinnitus (i.e., subjective tinnitus) perceived by the user to generate a virtual tinnitus object (i.e., tinnitus avatar). In addition, a virtual environment object (i.e., tinnitus background) corresponding to a sound source occurring in the virtual environment may be generated. To generate the virtual tinnitus object, location/size/rotation information of an object corresponding to a generation source of tinnitus noise occurring in the virtual environment may be used. To generate the virtual environment object, location/size/rotation information of an object corresponding to one or more sound sources occurring in the virtual environment may be used. This information may be stored in the storage unit.

The tinnitus perceived by each user may occur differently, such as metal scraping sound, bee sound, or wind sound. Accordingly, a process of matching frequency and loudness to correspond to (i.e., to be customized to) the subjective tinnitus perceived by the user may be performed in advance.

Meanwhile, according to an embodiment, the virtual tinnitus object and virtual environment object unit 130 may visualize the tinnitus avatar based on the subjective tinnitus information provided by the user. For example, when the user feels noise such as a mobile phone vibrating sound as tinnitus, the virtual tinnitus object and virtual environment object unit 130 may generate a vibrating mobile phone image as a tinnitus avatar. However, since the tinnitus felt by the user generally has only auditory information with no visual information, it is difficult to obtain direct visual information from the user to generate the tinnitus avatar. In this case, one of the preset images may be selected and set as the tinnitus avatar.

A virtual tinnitus avatar and virtual environment object generated by the virtual tinnitus object and virtual environment object unit 130 may be inserted and displayed at a preset location in the VR video by the VR video control unit 110.

The surround sound processing unit 140 may perform 3D sound processing to allow the user to perceive the location of the tinnitus avatar and the location of the virtual environment object. For this purpose, the time, loudness, and pitch of the sound of the sound output units on both sides are determined using the location information/rotation information of the tinnitus avatar and the location information/rotation information of the left and right sound output units constituting the sound output unit 160.

For this purpose, the surround sound processing unit 140 is implemented as a head-related transfer function (HRTF) of the Google resonance sound software development kit (SDK), and may be designed to generate spatial tinnitus sounds. The HRTF is a function that sets the time, loudness, and pitch of the sound according to the movement of the head.

As a result, the user simultaneously perceives the location of the tinnitus avatar and the location of the virtual environment object through ears, and the brain perceives a mixed sound in which the two sounds are mixed.

According to the embodiment, the size of the processed 3D sound may be adjusted according to the user's symptom. In addition, the type of the virtual environment object (i.e., tinnitus background) may be adjusted.

The user interface unit 150 may perform a function of transmitting commands or data input from the user or other external devices to other components of the tinnitus treatment device 100, and provide the user input signal to the VR video control unit 110. For example, the user interface unit 150 may refer to a series of means such as a keyboard, a joystick, and a touch panel for receiving input information from a user.

The sound output unit 160 is to individually provide 3D sound to the user's left and right ears. For example, the sound output unit 160 may be provided in the form of a headset that covers both ears of the user. Since the display unit is the HDM, the sound output unit may be thought of as headphones or speakers provided in such an HMD.

According to the embodiment, the sound output unit 160 may output the 3D sound only to an ear opposite to an ear where tinnitus occurs among the user's left and right ears. In other words, the sound output unit 160 may be implemented so that the 3D sound occurring on either the left or right side is not output to the other side. This is to increase treatment efficiency in an auditory area where tinnitus occurs.

The storage unit 170 stores the VR video, the tinnitus avatar, the tinnitus background, etc., and may be implemented as non-volatile memory such as flash memory or volatile memory such as dynamic RAM (DRAM), but is not limited thereto.

Figure 2:
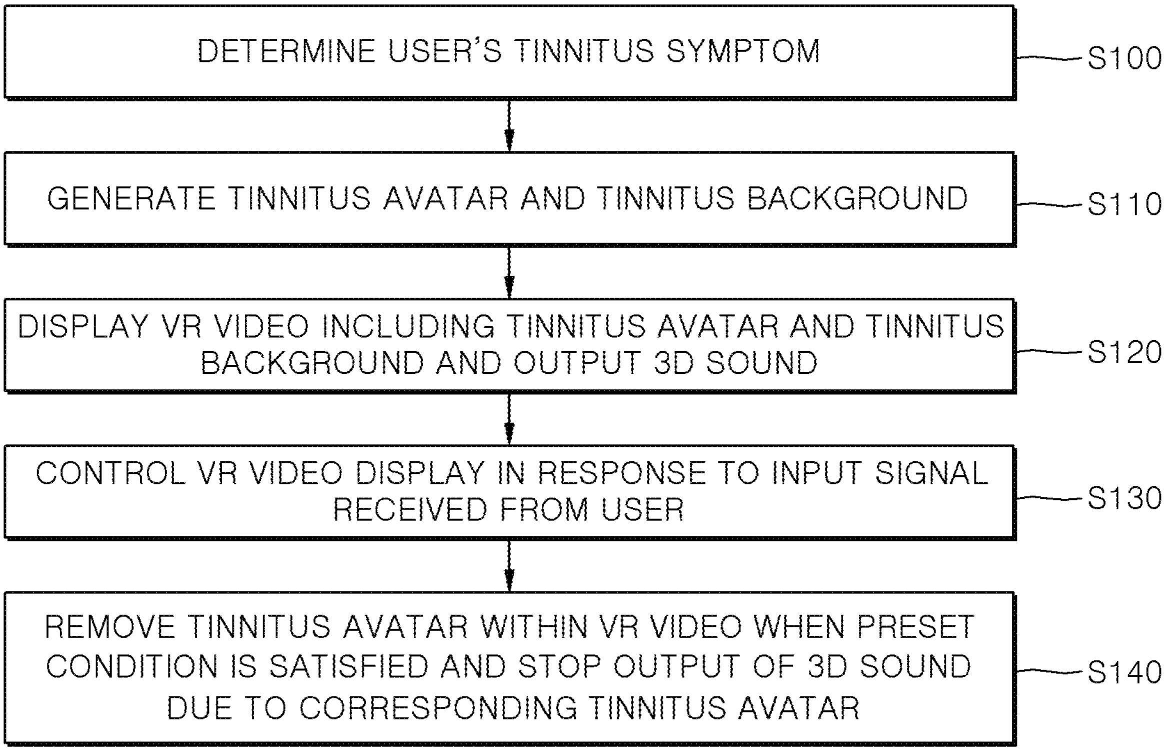
FIG. 2 is a flowchart for describing an operation of a tinnitus treatment device according to an embodiment.

FIG. 2 is a flowchart for describing an operation of the tinnitus treatment device according to an embodiment.

Referring to FIG. 2, the tinnitus treatment device 100 may receive the subjective tinnitus information related to the user's tinnitus symptom from the user or an assistant to determine the user's tinnitus symptom (S100). Here, the subjective tinnitus information may include information on a type (e.g., Beebp, buzz, crickets, mechanism, ocean, Whoosh, Wind_Noise, etc.) of noise felt by a user, whether tinnitus occurs in the left or right auditory area (e.g., bilateral tinnitus, unilateral tinnitus, etc.), occurrence frequency (e.g., every few seconds, every few minutes, continuous, etc.), tinnitus magnitude (e.g., 40 dB, 45 dB, 50 dB, 55 dB, 60 dB, 65 dB, 70 dB, etc.), etc. This is a kind of customizing step.

Figure 3:
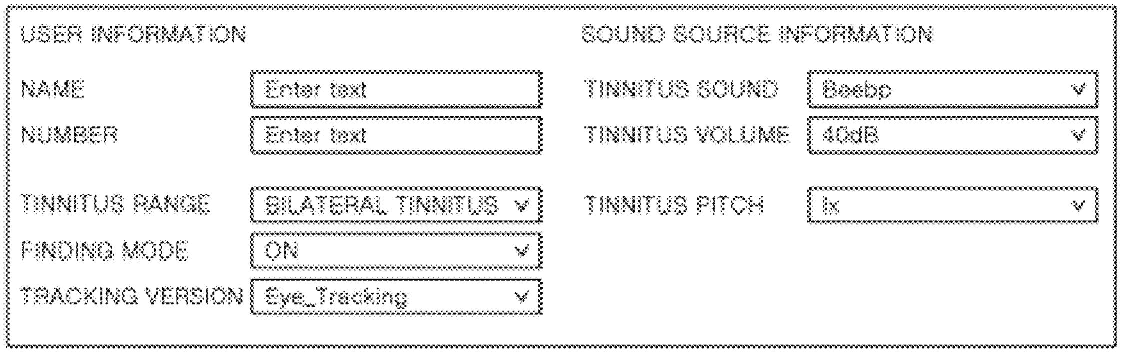
FIG. 3 is a diagram illustrating an implementation example of receiving subjective tinnitus information according to an embodiment.

The reception of the subjective tinnitus information may be achieved through a user interface such as a keyboard, a joystick, and a touch panel (an example of receiving the subjective tinnitus information through the touch panel is shown in FIG. 3).

The tinnitus treatment device 100 may generate the tinnitus avatar and the tinnitus background based on the subjective tinnitus information (S110).

The tinnitus treatment device 100 may insert and display the tinnitus avatar and the tinnitus background at a preset location in the VR video, and output the 3D sound corresponding to the tinnitus avatar and the tinnitus background (S120).

The tinnitus treatment device 100 may control the display of the VR video in response to the input signal received from the user (S130). For example, when the user wants to move within the VR video, the tinnitus treatment device 100 may display the VR video in which a user's viewpoint has been moved in response to the input signal.

The tinnitus treatment device 100 may remove the tinnitus avatar from the VR video when preset conditions are satisfied, and at the same time stop the output of the 3D sound by the tinnitus avatar (S140). The tinnitus treatment method according to an embodiment is achieved by the user's active participation, rather than passively training the user to provide and stop noise.

Here, the preset conditions may be set such that the user finds and moves the location of the tinnitus avatar within the VR video, puts the tinnitus avatar into a trash can object through the user interface, performs an arbitrary operation, or the like.

In other words, when the preset conditions are satisfied by the user's active action, the tinnitus treatment device 100 may remove the tinnitus avatar from the VR video, and at the same time stop the output of the 3D sound due to the tinnitus avatar, thereby allowing the user to achieve both the visual tinnitus blocking effect and auditory tinnitus blocking effect.

Figure 4:
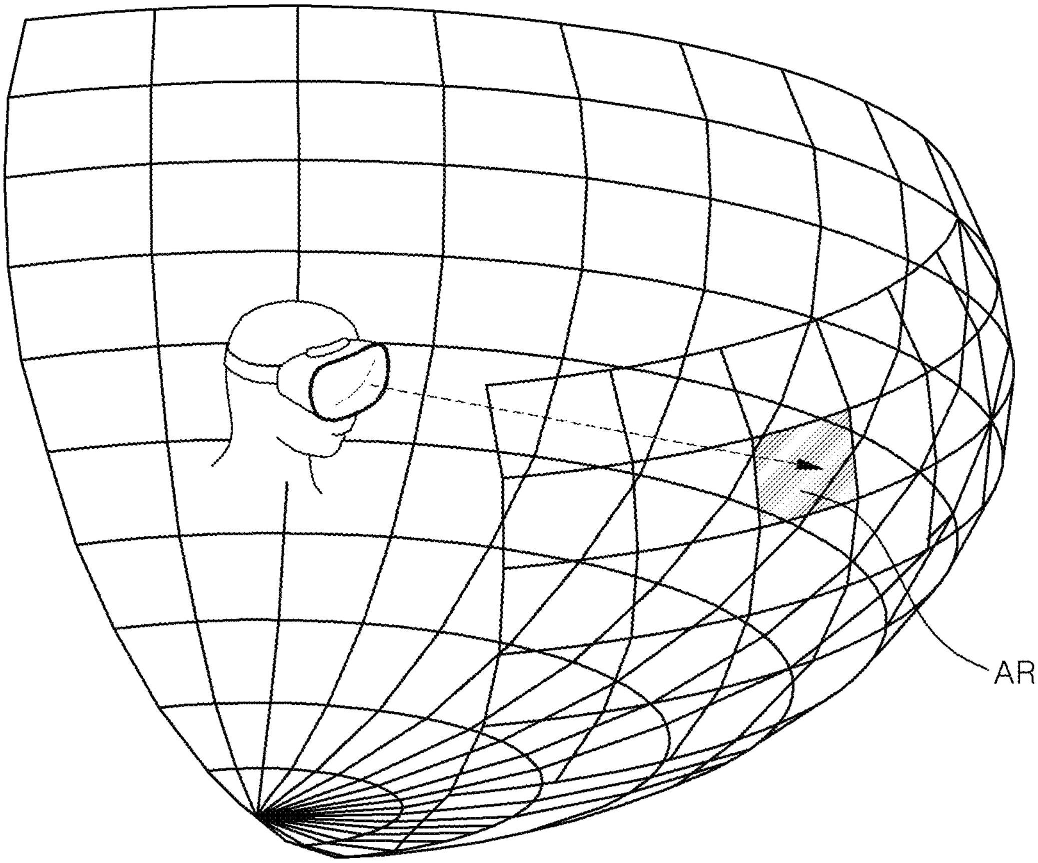
FIG. 4 is a diagram for describing a method of determining a viewpoint of a user wearing a tinnitus treatment device according to an embodiment.

FIG. 4 is a diagram for describing a method of determining a viewpoint of a user wearing a tinnitus treatment device according to an embodiment.

Referring to FIG. 4, since the tinnitus treatment device 100 implemented as the HMD device is worn on the user's head, the change in the user's gaze AR may be estimated according to the movement of the tinnitus treatment device 100. Basically, the HMD device are equipped with a sensor module, and the sensor module may detect the movement of the HMD device and output the detected movement as information such as x-coordinate, y-coordinate, z-coordinate, pitch, and roll.

The HMD device may detect a direction of the gaze AR based on the output information and configure a background video corresponding to the gaze AR. The background video may vary depending on a viewing angle provided by the HMD device, and the viewing angle may vary depending on specifications of a projector and optical system of the HMD device.

Therefore, the HMD device may obtain a direction of view (DoV) from a focus point based on the information output from the sensor module, and implement the background video in a virtual space according to a field of view angle FoV that a projection module can provide from the center of the gaze AR.

Figure 5:
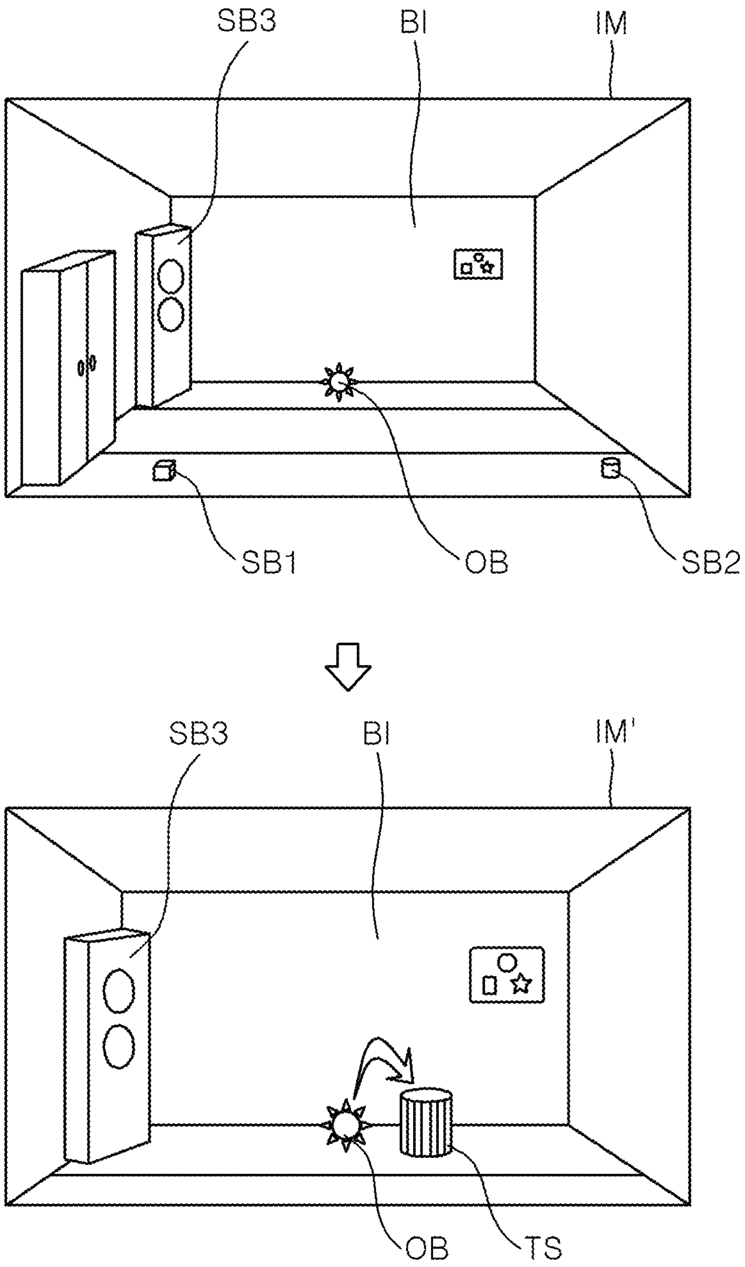
FIG. 5 is a diagram for describing a tinnitus treatment method using a surround sound virtual reality interface according to an embodiment.

FIG. 5 is a diagram for describing a tinnitus treatment method using a surround sound virtual reality interface according to an embodiment.

Referring to FIG. 5, the tinnitus treatment device 100 may display a VR video IM including a tinnitus avatar OB and tinnitus backgrounds SB1, SB2, and SB3. In the VR video, a background video BI is displayed so that the user may feel the virtual environment as if it were a real environment, and the tinnitus avatar OB may be displayed as an object that does not cause discomfort in the background video. The objects SB1, SB2, and SB3 corresponding to the tinnitus background may allow a user to perceive the mixed sound with the subjective tinnitus, and increase the difficulty in the process of the user finding the tinnitus avatar OB, thereby increasing the treatment effect.

The tinnitus treatment device 100 may display the VR video, and at the same time output the 3D sound, and control the output of the 3D sound in consideration of the distance between the user and the tinnitus avatar OB, the distance between the user and the tinnitus backgrounds SB1, SB2, and SB3, and the sensitivity of the left or right ears depending on the user's viewpoint.

The tinnitus treatment method by the tinnitus treatment device 100 is for removing or relieving the tinnitus symptom through the user's active participation, and the tinnitus treatment device 100 may task the user to find the tinnitus avatar OB within the VR video and the user may provide the input signal through the user interface unit 150 to change the display of the VR video.

When the tinnitus treatment device 100 provides the user input signal to allow the user to move forward, the tinnitus treatment device 100 may display a VR video IM' at the time when the user moves forward. As the viewpoint moves, the VR video changes and the output of the 3D sound also changes. In other words, the tinnitus treatment device 100 increases the output of the 3D sound due to the corresponding tinnitus avatar and/or the 3D sound due to the corresponding tinnitus background as the user approaches the tinnitus avatar OB and/or the tinnitus backgrounds SB1, SB2, and SB3 within the 3D image. For example, when changing from IM to IM', the 3D sound due to the tinnitus avatar OB becomes louder in both the left and right sides, and the 3D sound due to the tinnitus background SB3 becomes louder in both the left and right sides, and the 3D sound due to the tinnitus backgrounds SB1 and SB2 may be very small or disappear.

The tinnitus treatment device 100 may control the tinnitus avatar OB in response to the user input signal. When the user removes the tinnitus avatar OB by putting the tinnitus avatar OB in a trash can object TS within the VR video, the tinnitus treatment device 100 stops the output of the 3D sound due to the corresponding tinnitus avatar OB. Instead of stopping the output of the 3D sound, an embodiment that reduces the sound output to a very small level is also possible. Meanwhile, it is to be noted that the output of the 3D sound due to the tinnitus background SB1, SB2, and SB3 that has not been removed does not stop, and the output of the 3D sound appropriate for the location information/rotation information continues.

FIGS. 6A to 6E are diagrams for describing a tinnitus treatment method using a surround sound virtual reality interface according to another embodiment. The description will mainly focus on the differences from the above-described FIG. 5.

Figure 6A:
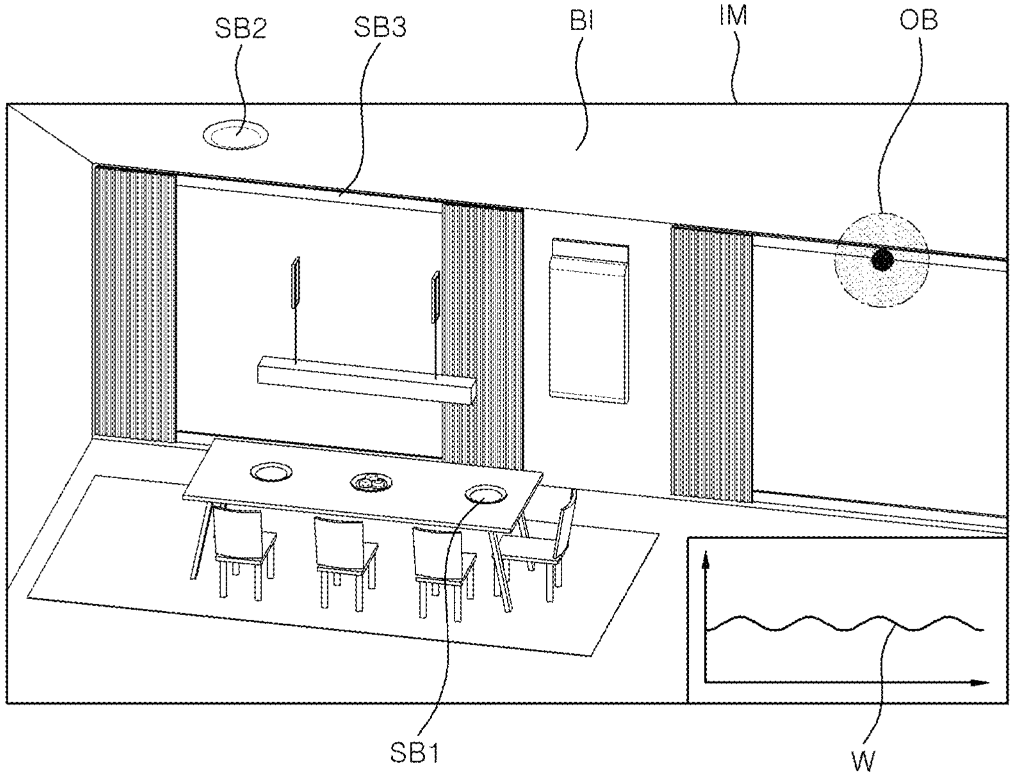
FIGS. 6A to 6E are diagrams for describing a tinnitus treatment method using a surround sound virtual reality interface according to another embodiment.

Referring to FIG. 6A, the tinnitus treatment device 100 may display the VR video IM including the tinnitus avatar OB, the tinnitus backgrounds SB1, SB2, and SB3, and the background video BI, and control the output of the 3D sound that is the mixed sound in which the 3D sound due to the tinnitus avatar and the 3D sound due to the tinnitus background are mixed. In this case, the tinnitus avatar OB may appear at a random location in the background video BI.

Figure 6B:
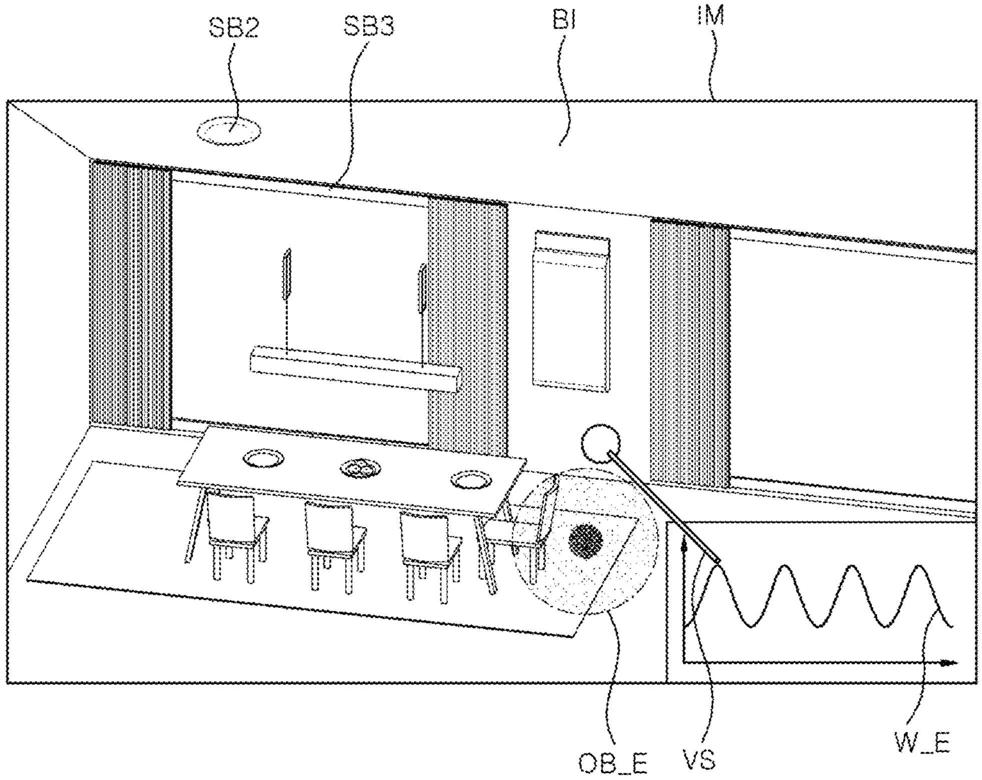
Figure 6C:
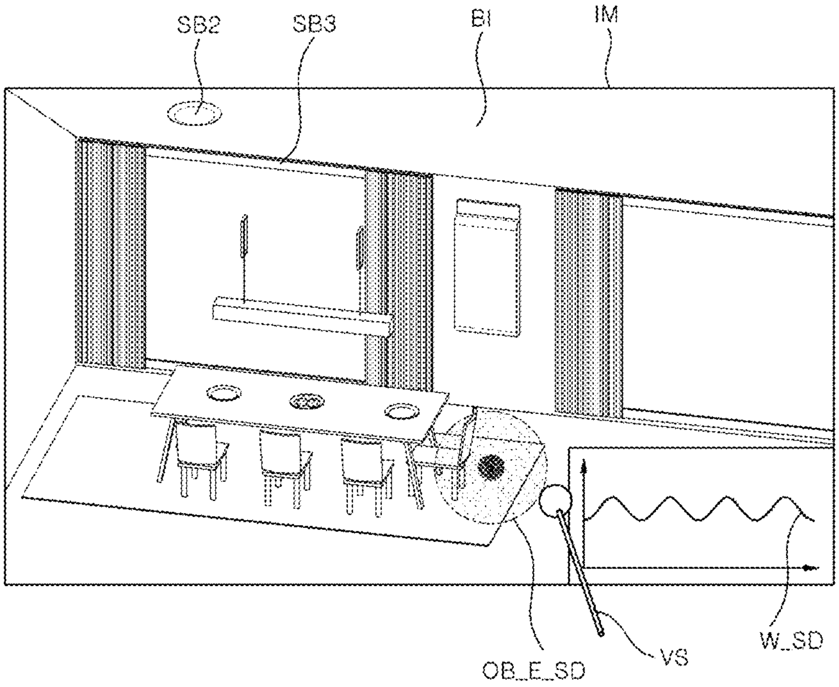

When the user changes the viewpoint and provides the user input signal to gaze at the tinnitus avatar OB for more than a certain period of time (for example, 5 seconds), the tinnitus treatment device 100 may hold the tinnitus avatar OB as a virtual tool VS in a video and display the tinnitus avatar OB in the state in which the tinnitus avatar OB is placed in the center (in FIG. 6B, tinnitus avatar OB_E is shown in a larger form compared to FIG. 6A). In this state, the output of the 3D sound due to the tinnitus avatar is increased according to the change in the location of the tinnitus avatar (random location→center) (In FIG. 6B, a graphic interface W showing the output of the 3D sound as a waveform is shown, and it can be seen that the waveform has become larger compared to FIG. 6A). Meanwhile, since only the tinnitus avatar is held and placed in the center, the 3D sound due to the tinnitus background may be maintained in its original state.

The tinnitus treatment device 100 may control the tinnitus avatar OB_E in response to the user input signal. When the user removes at least partially an edge of the tinnitus avatar OB_E using the virtual tool VS within the VR video, the output of the 3D sound due to the tinnitus avatar OB_E will also be reduced accordingly (In FIG. 6C, a tinnitus avatar OB_E_SD is illustrated to have become smaller due to the edge being cut compared to FIG. 6B, and it can be seen that the amplitude of an output waveform W of the 3D sound has also decreased compared to FIG. 6B).

Figure 6D:
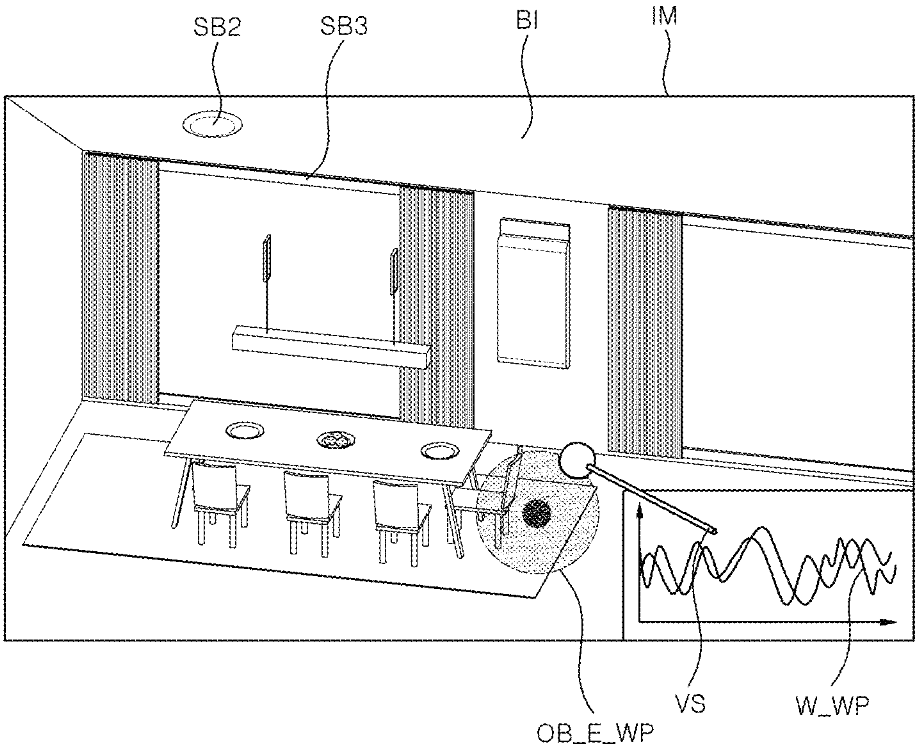

In this case, in order to intuitively transfer the cutting process to the user, as illustrated in FIG. 6D, the edge of the tinnitus avatar may be displayed as distorted by the virtual tool VS (referred to as OB_E_WP), and the output waveform of the 3D sound also becomes irregular, and thus, the sound similar to the cutting sound may be output (referred to as W_WP).

According to an embodiment, in the case of removing the edge by cutting the edge in a total of three levels, when the edge of the tinnitus avatar is firstly cut using the virtual tool, the tinnitus avatar is displayed with a size reduced by one level, and at the same time the output of the 3D sound due to the tinnitus avatar is also reduced by one level accordingly. To be continued, when the edge of the tinnitus avatar is further cut off secondly using the virtual tool, the tinnitus avatar is displayed with one size smaller than before, and at the same time the output of the 3D sound by the tinnitus avatar is also reduced by one level accordingly. Next, when the edge of the tinnitus avatar is thirdly cut off using the virtual tool, the tinnitus avatar is displayed with one size smaller than before, and at the same time the output of the 3D sound by the tinnitus avatar is also reduced by one level accordingly. It is preferable that the degree to which the output of the 3D sound is reduced step by step from the first to third is reduced to a sufficient level so that users may perceive that the tinnitus has been reduced due to their actions (i.e., by moving the virtual tool) (for example, 70 dB at first, 50 dB when reduced firstly, 30 dB when reduced secondly, 10 dB when reduced thirdly, etc.).

Figure 6E:
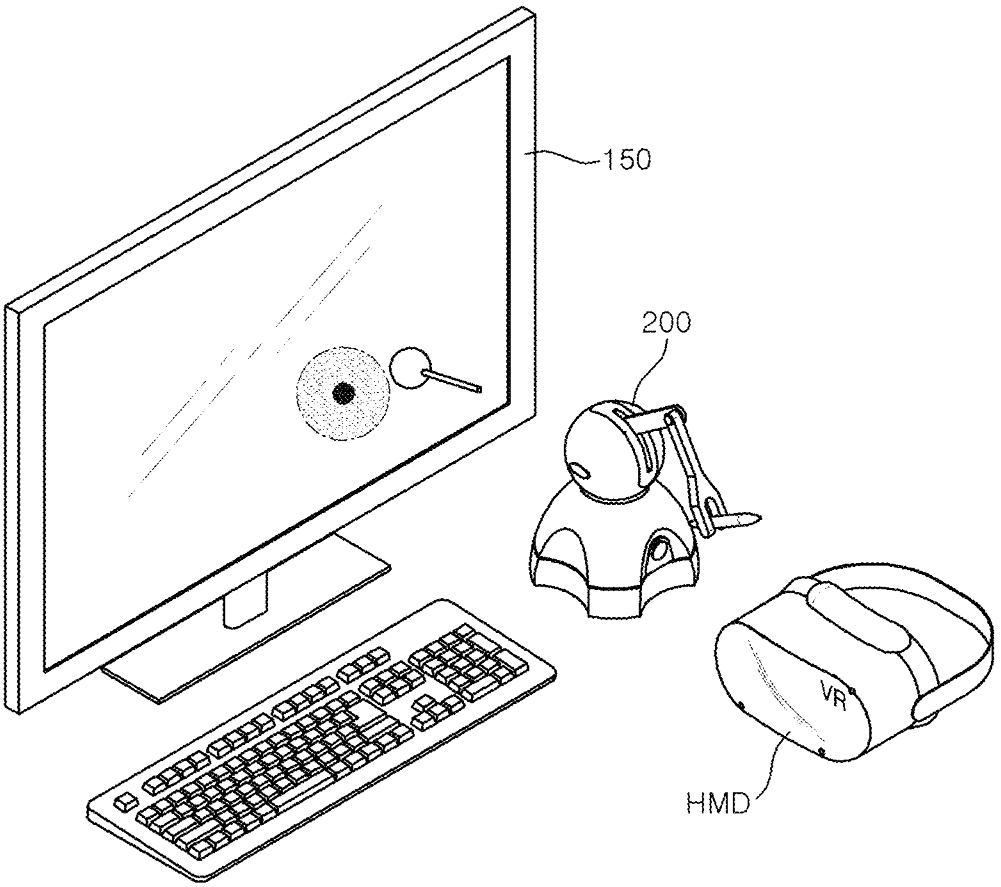

Meanwhile, the above-described virtual tool VS may be linked to a haptic device or a phantom haptic device 200 (see FIG. 6E). As a result, a user wearing an HMD may use the phantom haptic device to move the above-described virtual tool by his or her own actions while receiving visual and auditory information according to the movement of the head through the HMD. In addition, when the user cuts the tinnitus avatar, the user may receive the tactile sensation as if he/she directly cuts the tinnitus avatar using the phantom haptic device. This makes the tinnitus treatment possible through hyper-reality (multisensory sensation) to which the tactile function is added.

In this way, the tinnitus treatment device 100 according to an embodiment is not passively trained by providing and stopping noise to a user, but may be achieved through the user's active participation and through two-way interaction with the user to increase the tinnitus treatment efficiency.

Figure 7:
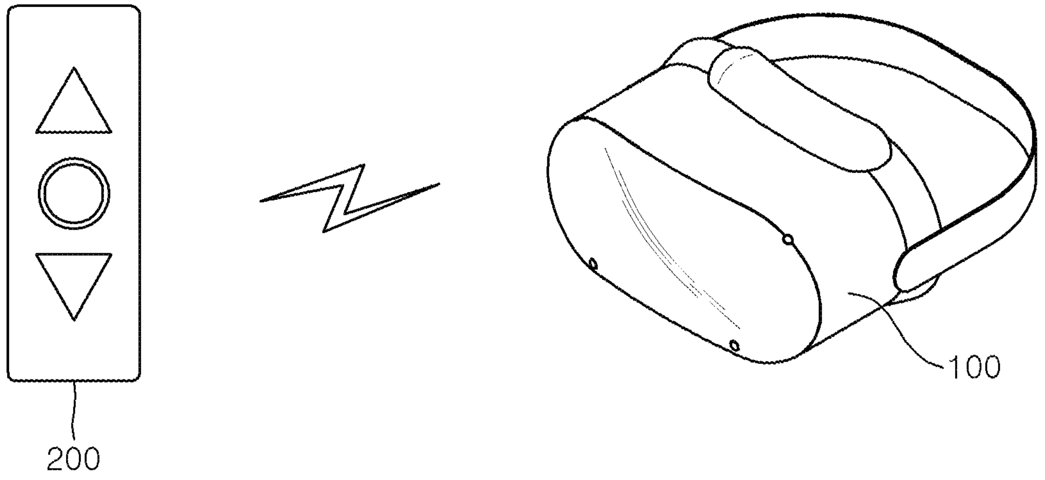
FIG. 7 is a diagram of a tinnitus treatment system using a surround sound virtual reality interface according to an embodiment.

FIG. 7 is a diagram of a tinnitus treatment system using a surround sound virtual reality interface according to an embodiment.

Referring to FIG. 7, the user may input the user input signal through the user interface unit 150 (see FIG. 1) mounted on the tinnitus treatment device 100, but provide the user input signal to the tinnitus treatment device 100 through a separate VR video controller 200. It may be considered that the separate VR video controller exists in addition to or in place of the user interface unit described above in FIG. 1.

The VR video controller 200 may include a button for moving the user forward and backward, and a button for displaying actions such as putting or throwing the tinnitus avatar in the trash can object, but is not limited thereto, and may include a series means for receiving the user input information. For example, the VR video controller may be the haptic device or the phantom haptic device that may transmit the user's hand movement as input and provide a specific tactile sensation to the user as output.

The VR video controller 200 and the tinnitus treatment device 100 may transmit and receive data through wired or wireless communication, and may transmit and receive data through, for example, short-distance communication (such as Bluetooth, Wi-Fi, etc.).

In this way, according to one embodiment, a user (patient) looking in the VR can confirm a virtual object in which the tinnitus treatment sound is heard in the virtual environment through the surround sound (i.e., 3D sound). In other words, the virtual object of the tinnitus can be confirmed through a visual virtual object, and an interface that may confirm the location through the surround sound is provided.

As described above, the surround sound virtual reality interface may include a virtual tinnitus object and virtual environment object unit that has location/size/rotation information of the object corresponding to a generation source of tinnitus noise in the virtual environment and location/size/rotation information of an object corresponding to a sound source occurring in the virtual environment, a surround sound processing unit that receives location information/rotation information of the virtual tinnitus object and the location/rotation information of the sound output units on both sides (left and right) and sets the time, loudness, and pitch of the sound of the sound output units on both sides, and a VR video control unit that controls the sound setting value in the surround sound processing unit to output the sound to the sound output units on both sides and the visual information in the virtual tinnitus object and virtual environment object unit to output the image to the display unit.

As a result, the surround sound virtual reality interface may allow the surround sound processing unit to calculate the time, loudness, and pitch of the sound in real time according to the change in the location/size/rotation information of the virtual tinnitus object and the virtual environment object. The surround sound software produced based on the HRTF, which is the function that sets the time, loudness, and a pitch of the sound according to the movement of the head, may be applied. The location/size/rotation information of the virtual tinnitus objects and the virtual environment objects may be detected and moved or changed due to other virtual objects. The rotation/rotation information of the sound output units on both sides may vary depending on the movement of the user's head. The changed location/size/rotation information of the virtual tinnitus objects and the virtual environment objects may be output the image to the display unit and the sound to the sound output units on both sides.

For this, the surround sound virtual reality interface may be implemented as the following key components. First, the computer and virtual reality device perform calculations so that a user visually outputs the virtual tinnitus object and virtual reality object and auditorily outputs the virtual tinnitus object and virtual reality object, and the tinnitus object is located at the virtual location. In this way, the sound of the virtual reality may be visualized as the virtual object, and the sense of immersion may be auditorily given as if the virtual object is in a virtual location. Second, the surround sound software calculates the user's location and the virtual tinnitus location and calculates the sound of the sound output units on both sides so that the user may auditorily know the location. As a result, not only is it possible to auditorily perceive the location of the virtual tinnitus object, but it is also possible to increase the sense of immersion in the virtual reality by ensuring that the tinnitus is heard at a specific location.

EXPERIMENTAL EXAMPLE

In this study, the feasibility of VR was assessed in a patient with chronic subjective tinnitus. The assessment of the clinical benefit was performed based on patient electroencephalogram (EEG) analysis and questionnaire responses after 6 to 8 weeks after a patient participates in a VR-based relief program. The clinical trial was performed in a tertiary referral hospital. Nineteen patients (33 to 64 years old) who visited the hospital with chronic subjective tinnitus for more than 3 months were enrolled in the study. The intervention is configured to discard the tinnitus avatar in the VR. It was expected that patients would feel like they have subjective feeling of control over the tinnitus with this intervention. The VR environment is composed of four sessions in four settings: bedroom, living room, restaurant, and city street. The myogenic activity change in a prefrontal area associated with the tinnitus in the patient was analyzed using standardized low-resolution brain electron tomography. After the VR-based tinnitus treatment program, the tinnitus handicap inventory (THI), total score (50.11 to 44.21, $P=0.046$), and grade (3.16 to 2.79, $P=0.035$) were improved significantly ($P<0.05$). The Pittsburgh sleep quality index also showed the improved result ($P=0.025$). On the other hand, there was no significant change after the intervention in the tinnitus handicap questionnaire, quality of life assessment (WHOQOL), hospital anxiety and depression scale (HAD Scale), and profile of mood states. Baseline EEG data showed that brain activity in orbitofrontal cortex was significantly increased in alpha and theta frequency bands. In addition, a patient with improved THI scores after the intervention showed the specific increase in brain activity for theta and high beta bands in the orbitofrontal cortex. The results of this study suggest that virtual reality-based programs, as part of cognitive behavioral therapy, may help alleviate tinnitus-related pain in a patient with chronic subjective tinnitus.

The VR system may provide users with the sense of presence and immersion through 360° visual display, spatial acoustics, and haptic feedback. This realistic user experience suggests that the VR may be a viable clinical treatment method. This study aimed to provide a sense of control that may lead to tinnitus relief by allowing a patient to manipulate and remove objects (VR avatar) that generate tinnitus sound in a VR environment. The patient indicates and explores the tinnitus avatar and, furthermore, actually getting rid of the tinnitus avatar by holding the tinnitus avatar and throwing the tinnitus avatar into the trash can. Therefore, patients feel that he/she may control over tinnitus by erasing the tinnitus avatar.

After the completion of the experiment, we assessed that the effect of this VR-based intervention for treating a patient with tinnitus using questionnaires, electroencephalogram (EEG), and standardized low-resolution brain electromagnetic tomography (sLORETA). The change in the auditory and non-auditory cortical or subcortical network could be assessed through the analysis of the participant's EEG data collected before and after the program. Through this process, this study sought to determine the usefulness of VR as a selective treatment method for reducing the tinnitus and related symptoms.

Method

Patient and Questionnaire

Among patients (19 to 80 years old) who visited a hospital with tinnitus as a main symptom, patients who had chronic nonpulsatile tinnitus for more than 3 months, were able to communicate smoothly in their native language, and agreed to participate in the study were selected. Patients who were frequently exposed to noise due to their occupation or hobby activities and patients who were expected to have difficulty operating the HMD-based VR program were excluded. Ultimately, 19 patients (9 men, 10 women) with tinnitus participated in this study.

The patient's medical history, demographic information, physical examination, and physical examination including vital signs (blood pressure, heart rate, temperature, and respiratory rate), weight, height, and daily living skills were assessed accordingly. In addition, before the study, after checking for underlying diseases and treatment history related to tinnitus, excluding tinnitus, neurological and psychological problems, for these patients, audiograms and tinnitus symptoms before and after the experiment were examined together to exclude cases related to unnecessary bias.

The patient status was assessed before and after the experiment through a questionnaire about tinnitus itself, including THI, THQ, and visual numeric scale (VNS), which are related to the severity of tinnitus-related pain. Although it is not designed as a result measurement, it is a simple, easily administered, psychometrically powerful measurement to assess the influence of tinnitus on daily life, and is widely used in national health systems. Questionnaires on tinnitus-related symptoms, including PSQI, WHO-QoL, POMS, HADS, etc., for depression, anxiety, and sleep disorders accompanying tinnitus were written. In addition, a simulator sickness questionnaire (SSQ) was administered to assess post-experimental patient symptoms that may occur after using the VR system.

Experimental Protocol

Figure 8A:
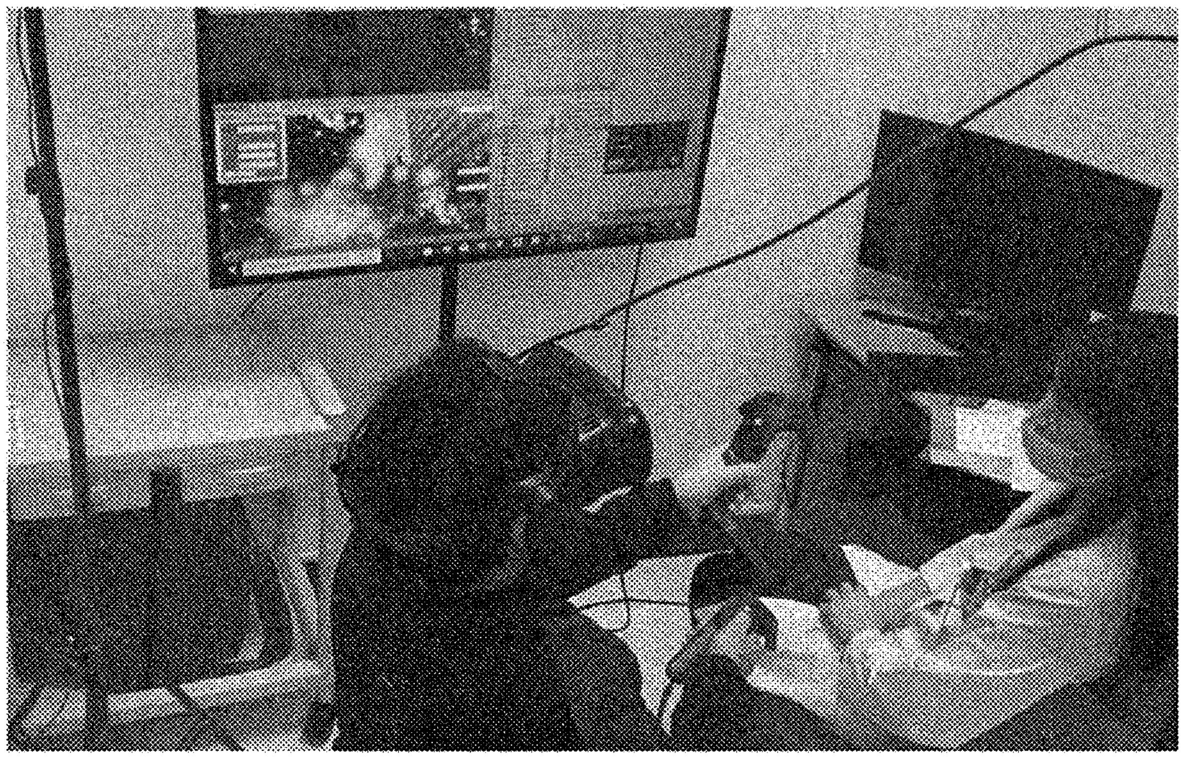
FIG. 8A illustrates that a patient and a clinician see a virtual environment through a head mounted display (HMD) and a screen, respectively. The patient listens to a spatial sound from a tinnitus avatar through a HMD headphone. The patient also uses a VIVE controller to move the tinnitus avatar.
Figure 8B:
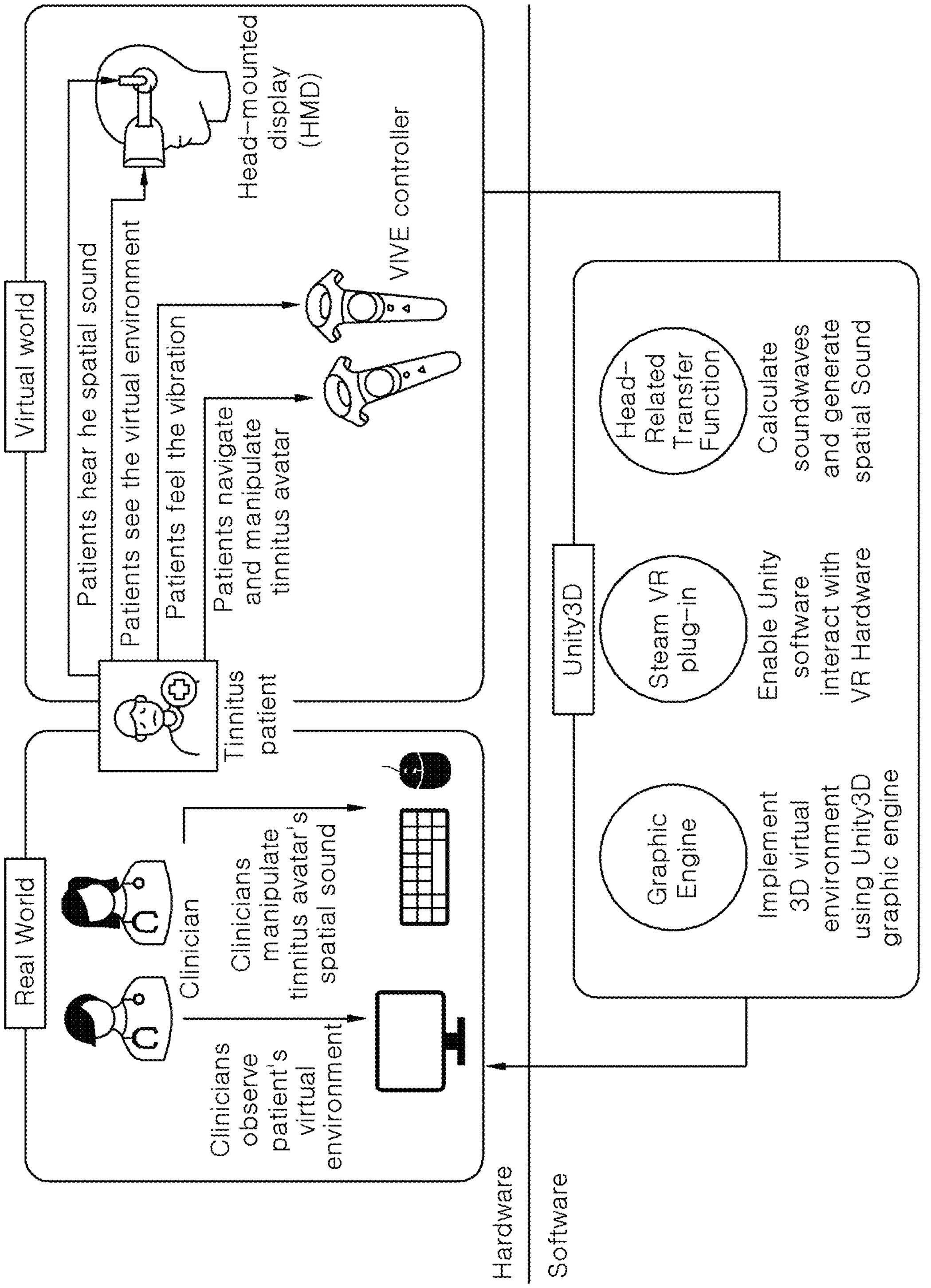
FIG. 8B illustrates hardware and software settings.
Figure 9:
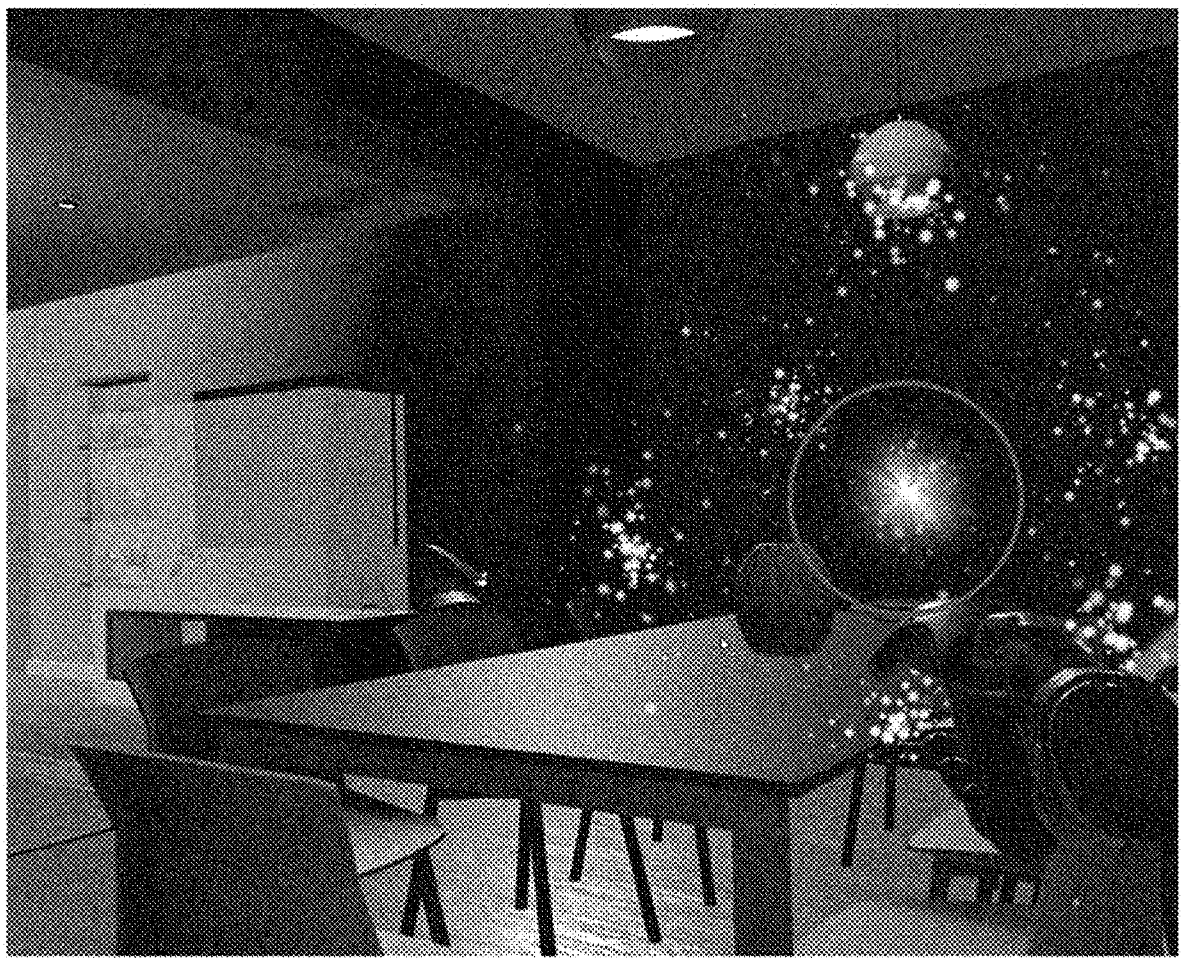
FIG. 9 is a diagram illustrating an example of a virtual environment for a treatment session according to an embodiment. In this case, a shiny object (red circle) emitting particles is a tinnitus avatar. A yellow area is a tinnitus processing location where the patient is instructed to discard the tinnitus avatar.

First, the tinnitus avatar was generated to mimic each patient's subjective tinnitus by matching the frequency and loudness. The acoustic modelization of perceived tinnitus established by a signal matches the spectrum and intensity of the patient's perception of tinnitus. This indicates that a fusion process may occur between the subjective tinnitus and the matched stimulus presented to the contralateral ear. A tutorial session was performed before a main treatment session. The tinnitus avatar is designed to generate spatial tinnitus sounds implemented with the HRTF of the Google resonance SDK. Participants learned how to move in a VR environment and how to perform tasks to process tinnitus avatar (see FIG. 8). The tinnitus avatar used the HRTF to generate five types of 3D tinnitus sounds: whistling, hissing, roaring, humming, and ringing. The participants should use their hearing to find the tinnitus avatar. The participants can move in the virtual environment by pressing an upper end and lower end of a trackpad on a left VIVE controller. When the participants approach within a certain distance, they may see the tinnitus avatar. When holding the tinnitus avatar by pressing a trigger button on a right VIVE controller, the color of the avatar changed and the vibration feedback was generated on the right VIVE controller to notify the participants that the tinnitus avatar was captured. Then, the participants moved the tinnitus avatar from a virtual environment scene to a tinnitus processing location (see FIG. 9). After discarding the tinnitus avatar, the tinnitus sound decreased dramatically. For the tinnitus VR intervention sessions, two sets of virtual environments were developed for each city's street, restaurant, living room, and bedroom scenes. The tinnitus processing location is placed in noisy scenes of each virtual set (i.e., a bedroom entrance, next to a television in a living room, an ordering counter in a restaurant, and a car hood on a city street), thereby creating a cognitive illusion that absorbs tinnitus sounds into much louder environmental noises. Three tinnitus avatar processing tasks were performed during each treatment session.

Figure 10:
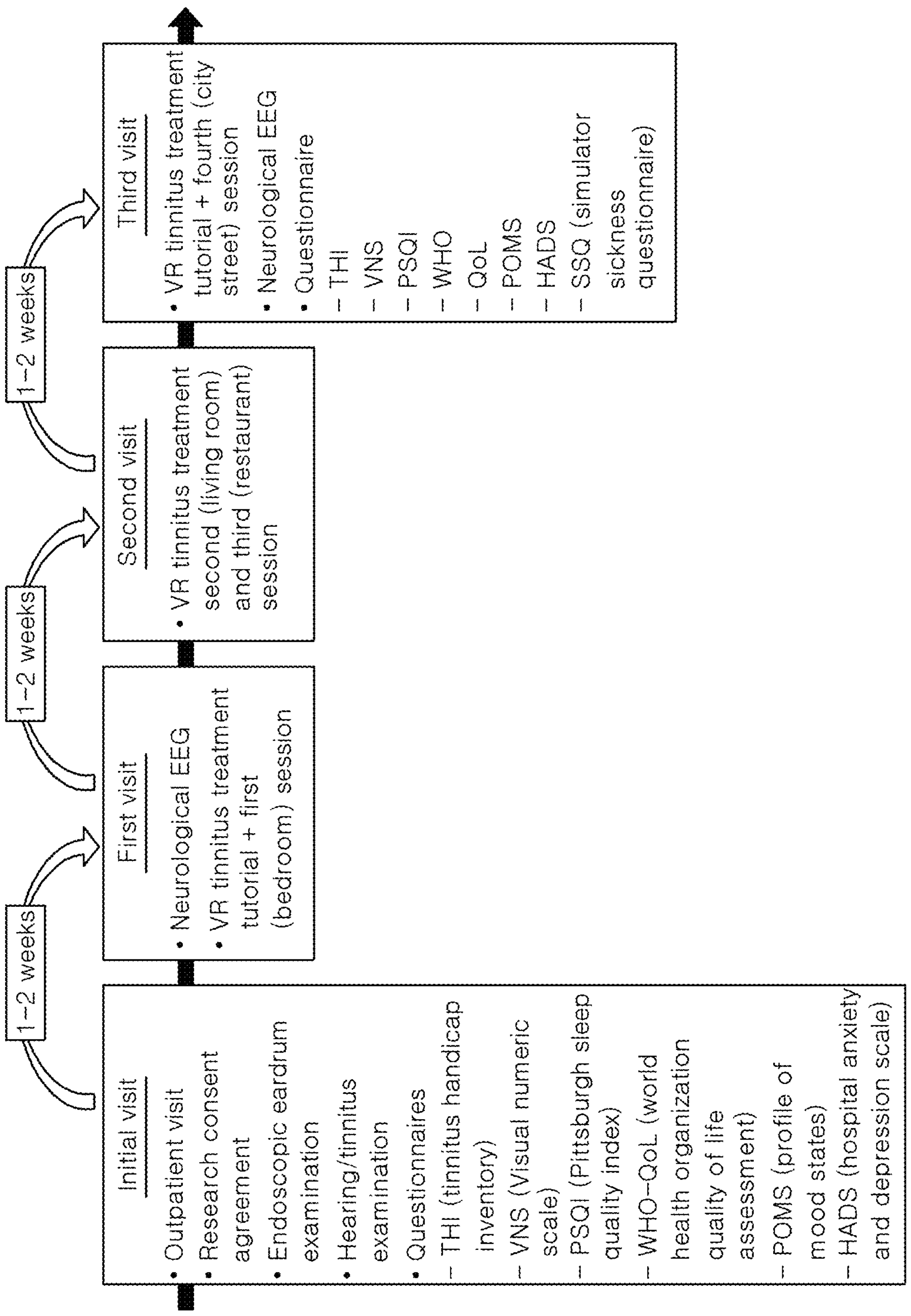
FIG. 10 is a diagram illustrating four steps of an experimental protocol according to an embodiment.
Figure 11:
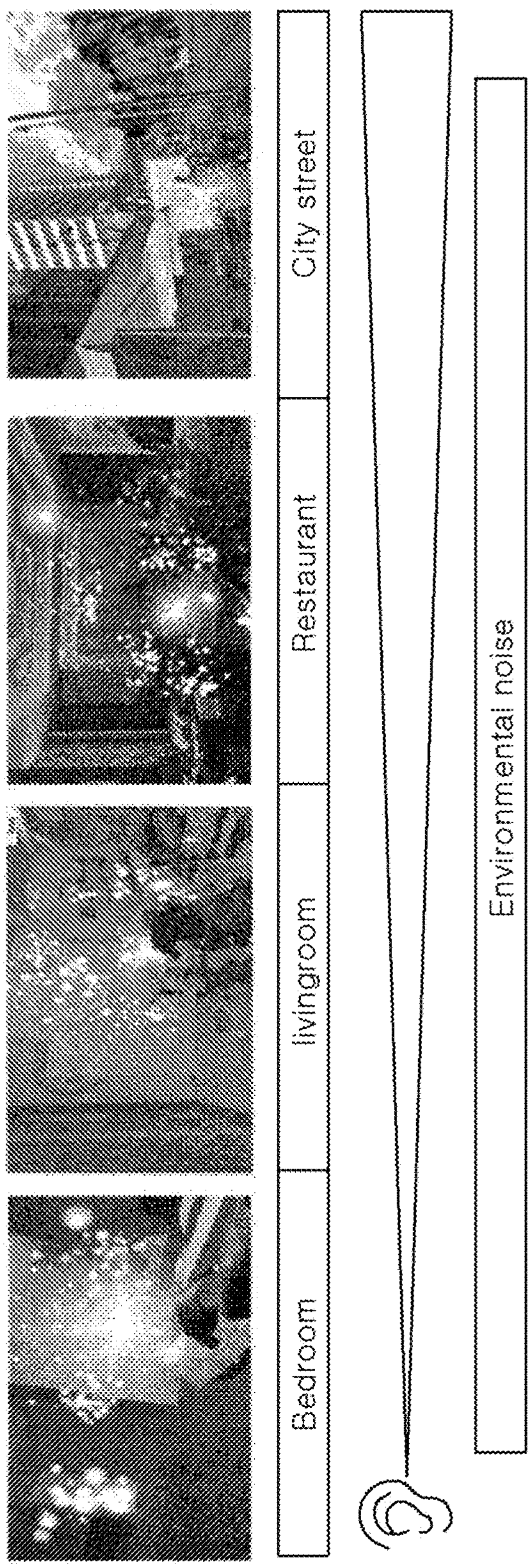
FIG. 11 is a diagram illustrating an example of a virtual reality tinnitus treatment scene according to an embodiment. In this case, the scenes are arranged based on increasing environmental noise from left to right. Participants experienced the scenes in a left to right order.

Patients visited a hospital four times and experienced the VR tinnitus intervention every 1 to 2 weeks (see FIG. 10). Those who agreed to participate in the experiment underwent endoscopic tympanic membrane examination and hearing/tinnitus examination on the first visit and then received a questionnaire. They experienced the VR tinnitus intervention system for a total of three sessions, from the first visit to the third visit. During the first visit, patients underwent electroencephalography to check their brain state before experiencing the VR tinnitus intervention system. The first session (city street) was followed by a tutorial session. The participants performed both the second (dining room scene) and third (living room scene) sessions on the second visit. They performed the fourth session (bedroom scene) on the third visit. The sessions were arranged to reduce a volume of environmental noise as the sequence progressed (see FIG. 11). After the fourth session is completed, the participants underwent the SSQ questionnaire and EEG test.

Source Localization Using sLORETA

This study used sLORETA software, which may analyze intracerebral electrical sources from scalp-recorded activity based on the EEG data. The EEG data was preprocessed and 30 epochs were prepared per participant. This epoch was analyzed over six frequency bands (delta, 1 to 4 Hz; theta, 4 to 8 Hz; alpha, 8 to 12 Hz; low beta, 12 to 18 Hz; high beta, 18 to 30 Hz; and gamma, 30 to 55 Hz). In the sLORETA, the source image was spatially modeled as a set of 6239 voxels (size 5×5×5 mm). These layers were obtained from amygdala, hippocampus, and cortical gray matter. The sLORETA data were based on reconstruction of digitized Montreal Neurological Institute (MNI) 152 coordinates into Talairach coordinates.

Ten ROIs were selected in the frontal area based on previous literature on tinnitus. Each ROI is composed of one or two Brodmann areas (Table 1: selected RIO and BA). In addition, the current source densities for each ROI were compared using SPSS.

TABLE 1

| ROI (Regions of Interest) | BA (Brodmann Areas) |
|---|---|
| Dorsal anterior cingulate cortex | 24L |
| | 24R |
| Pregenual anterior cingulate | 32L |
| | 32R |
| Subgenual anterior cingulate cortex | 25L |
| | 25R |
| Orbitofrontal cortex | 10L&11L |
| | 10R&11R |
| Dorsolateral prefrontal cortex | 9L&46L |
| | 9R&46R |

Result

The primary result measurement was the results of questionnaires about patient condition and loudness-related symptom before and after the experiment. The exploratory result measurement was current source densities for 10 ROIs. The results of the questionnaire result about VR sickness using the SSQ provided another measure.

Statistical Analysis

Descriptive statistics were used to analyze the results. The improvement in the THI score and tinnitus grade was reported using the change in difference with respect to the pretreatment measurement. The differences before and after the treatment were reported using absolute values. The statistical significance of the difference found in the questionnaire was assessed using a Wilcoxon signed-rank test. The absolute values before and after the treatment were paired for each participant, and the statistical significance was considered as p less than 0.05. All data were analyzed using SPSS (version 20.0; SPSS, Chicago, Illinois, USA). In addition, for the differences in the EEG data before and after the treatment in the ROI analysis, the Wilcoxon signed-rank test and Mann-Whitney U test between the EEG data before and after the treatment in subgroups divided by the THI score were performed. (THI<0: n=12, THI≥0: n=7). In this study, in order to investigate potential EEG indicators that may reflect the improvement in tinnitus-related pain at an exploratory level, multiple comparison correction was not performed and the significance level is considered to be 0.050.

Result

Patient Demographics and Clinical Characteristics

Nineteen patients with nonpulsatile tinnitus were selected for this study. The average participant age was 56.40 (±8.19) years. The participants had experienced tinnitus symptoms for an average of 7.34 years. Eight patients on each side, eight patients on the left side, and three patients on the right side experienced tinnitus. The average of the tinnitus loudness was 5.42 sensation level (SL). All types of tinnitus were studied without exclusion. None of the patients had Meniere's disease, eardrum-related disease, or other neurological conditions. Patients with psychiatric disorders were excluded from the study (Table 2: patient demographics and clinical characteristics).

TABLE 2

| Patients (n = 19) | Age (y) | Gender | Tinnitus laterality (Left/Right/Both ears) | Tinnitus duration (y) | Type of Tinnitus | Associated symptoms | Tinnitus Pitch Matching (Hz) | Tinnitus Loudness (SL) |
|---|---|---|---|---|---|---|---|---|
| Patient 1 | 55 | F | Both | 8 | Buzzing | Hearing loss | 500 | 10 |
| Patient 2 | 62 | M | Left | 0.3 | Ringing | None | 4000 | 5 |
| Patient 3 | 63 | F | Right | 5 | Ringing | Hearing loss | 2000 | 30 |
| Patient 4 | 51 | M | Left | 15 | Ocean waves | Hearing loss | 4000 | 0 |
| Patient 5 | 52 | M | Left | 2 | Ringing | Hearing loss, Dizziness, Ear fullness | 6000 | 5 |
| Patient 6 | 49 | F | Right | 1 | Whooshing | Hearing loss | 250 | −5 |
| Patient 7 | 64 | M | Both | 10 | Crickets | Hearing loss | 1000 | 0 |
| Patient 8 | 62 | F | Left | 13 | Static | Hearing loss, Dizziness | 8000 | 10 |
| Patient 9 | 58 | F | Both | 3 | Crickets | Hearing loss | 6000 | 0 |
| Patient 10 | 58 | F | Both | 10 | Whooshing | None | 8000 | 5 |
| Patient 11 | 43 | F | Both | 1 | Buzzing | Hearing loss, Dizziness | 4000 | 0 |
| Patient 12 | 63 | M | Both | 5 | Crickets | Hearing loss | 8000 | −5 |
| Patient 13 | 64 | F | Left | 13 | Ocean waves | None | 2000 | −10 |
| Patient 14 | 58 | M | Left | 0.25 | Ocean waves | Hearing loss | 8000 | −5 |
| Patient 15 | 53 | F | Both | 10 | Ringing | Dizziness | 8000 | 5 |
| Patient 16 | 57 | F | Both | 7 | Electrical | Hearing loss, Dizziness | 8000 | 5 |

TABLE 2-continued

| Patients (n = 19) | Age (y) | Gender | Tinnitus laterality (Left/Right/Both ears) | Tinnitus duration (y) | Type of Tinnitus | Associated symptoms | Tinnitus Pitch Matching (Hz) | Tinnitus Loudness (SL) |
|---|---|---|---|---|---|---|---|---|
| Patient 17 | 62 | M | Left | 30 | Buzzing | Hearing loss, Dizziness, Ear fullness | 4000 | 5 |
| Patient 18 | 64 | M | Left | 1 | Ringing | None | 8000 | 0 |
| Patient 19 | 33 | M | Right | 5 | Dial tones | Hearing loss | 4000 | 20 |
| Mean ± SD | 56.4 ± 8.19 | | | 7.34 ± 7.23 | | | | 5.42 ± 9.22 |

Analysis of Questionnaire Provided to Study Participants

Figure 12:
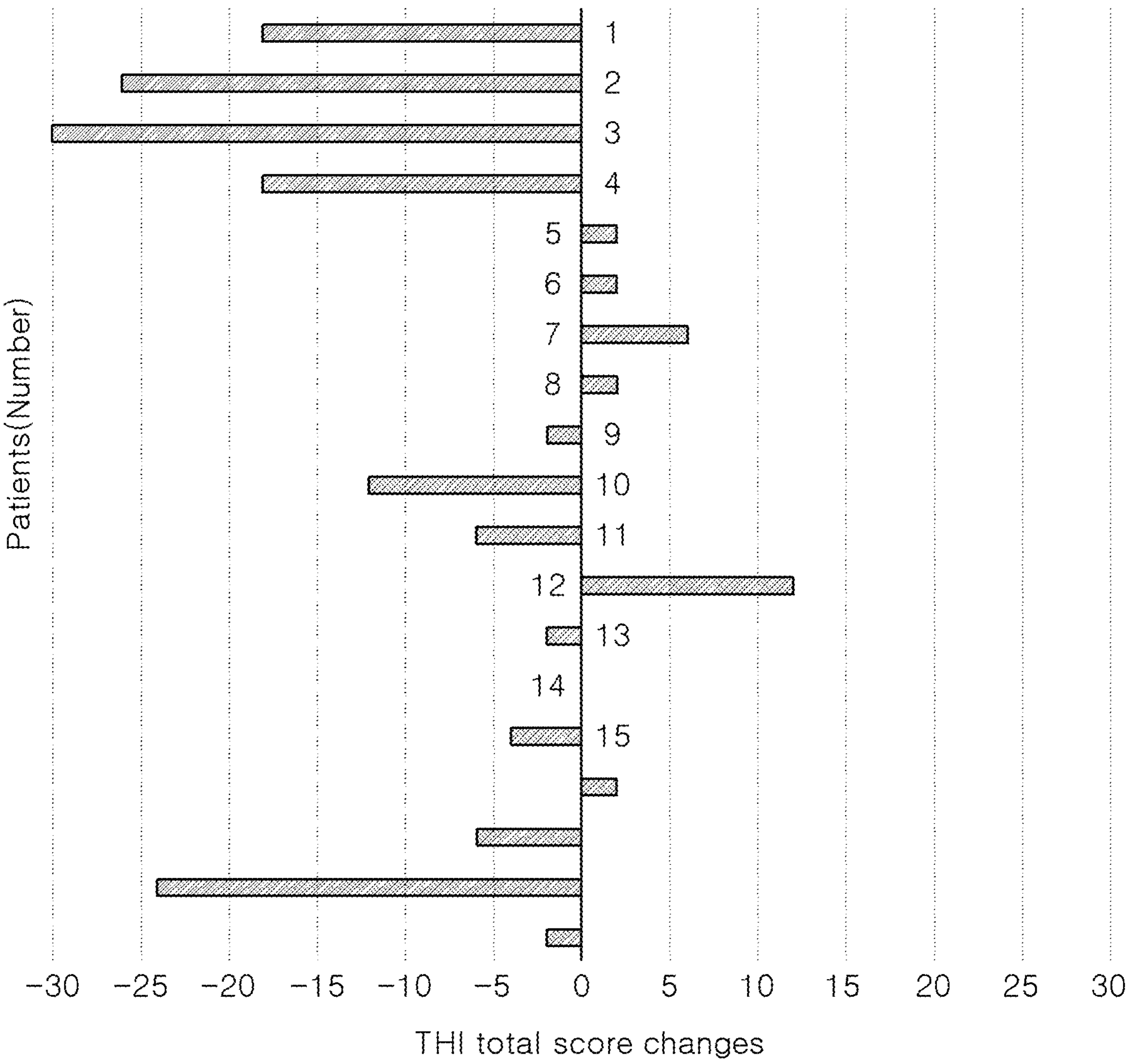
FIG. 12 is a diagram illustrating a change in total tinnitus handicap inventory (THI) score according to an embodiment. In this case, 12 out of 19 patients showed improvement in a total THI score.

Participants filled out the same tinnitus-related questionnaire before and after participating in the VR program. Tinnitus improved after the treatment based on the THI and PSQI, which are closely related to the tinnitus. Statistically significant differences were observed in THI functional score (P=0.005), total score (P=0.046), and grade (P=0.035) (Table 3: Results of questionnaires administered to study participants. THI: Tinnitus handicap inventory; PSQI: Pittsburgh sleep quality index; WHO-QOL: World Health Organization Quality of Life Assessment; HADS: Hospital Anxiety and Depression Scale, POMS: Profile of mood states). FIG. 12 illustrates the effect of tinnitus relief according to the change in an individual's total THI score before and after the program. Unlike statistically significant changes, clinically meaningful changes were defined as including a minimum of 7 points on THI33. In our sample, 6 of 19 patients met this threshold (37%). However, there was no correlation between the THI score and PSQI. Other questionnaires used to assess loudness-related symptom did not show statistically significant differences.

TABLE 3

| | Before VR | After VR | Difference | P value |
|---|---|---|---|---|
| THI | | | | |
| Functional scale | 22.00 | 17.00 | −5.00 | 0.005 |
| Emotional scale | 19.00 | 16.70 | −2.30 | 0.108 |
| Catastrophic scale | 10.00 | 10.00 | 0 | 0.968 |
| Total | 50.11 | 44.21 | −5.90 | 0.046 |
| Grade | 3.16 | 2.79 | −0.37 | 0.035 |
| PSQI | 8.47 | 7.37 | −1.10 | 0.025 |
| THQ | | | | |
| Somatic score | 49.40 | 44.45 | −4.95 | 0.198 |
| Emotional score | 41.00 | 38.00 | −3.00 | 0.257 |
| Social score | 60.00 | 60.00 | 0 | 0.727 |
| Total | 48.50 | 45.30 | −3.20 | 0.165 |
| QOL | 72.63 | 73.84 | +1.21 | 0.434 |
| HAD | | | | |
| Depression | 7.58 | 7.74 | +0.16 | 0.916 |
| Anxiety | 7.89 | 7.79 | −0.10 | 0.354 |
| POMS | 81.32 | 77.79 | +3.53 | 0.778 |

For SSQ34, the total score was calculated using the following equation. Total score=nausea score+eye movement score+disorientation×3.74. The nausea, eye movement, disorientation, and total scores for the present system were 48.20, 58.25, and 74.73, respectively (Table 4: Analysis of nausea, eye movements, disorientation, and total scores derived from the SSQ. sd: standard deviation). After applying weights, the total score was 32.81 points.

TABLE 4

| SSQ (Simulator Sickness Questionnaire) | | | |
|---|---|---|---|
| Nausea (sd) | Oculomotor (sd) | Disorientation (sd) | Total Score (sd) |
| 48.20 (33.97) | 58.25 (36.81) | 74.73 (60.63) | 32.81 (24.03) |

EEG Data Analysis

Figure 13:
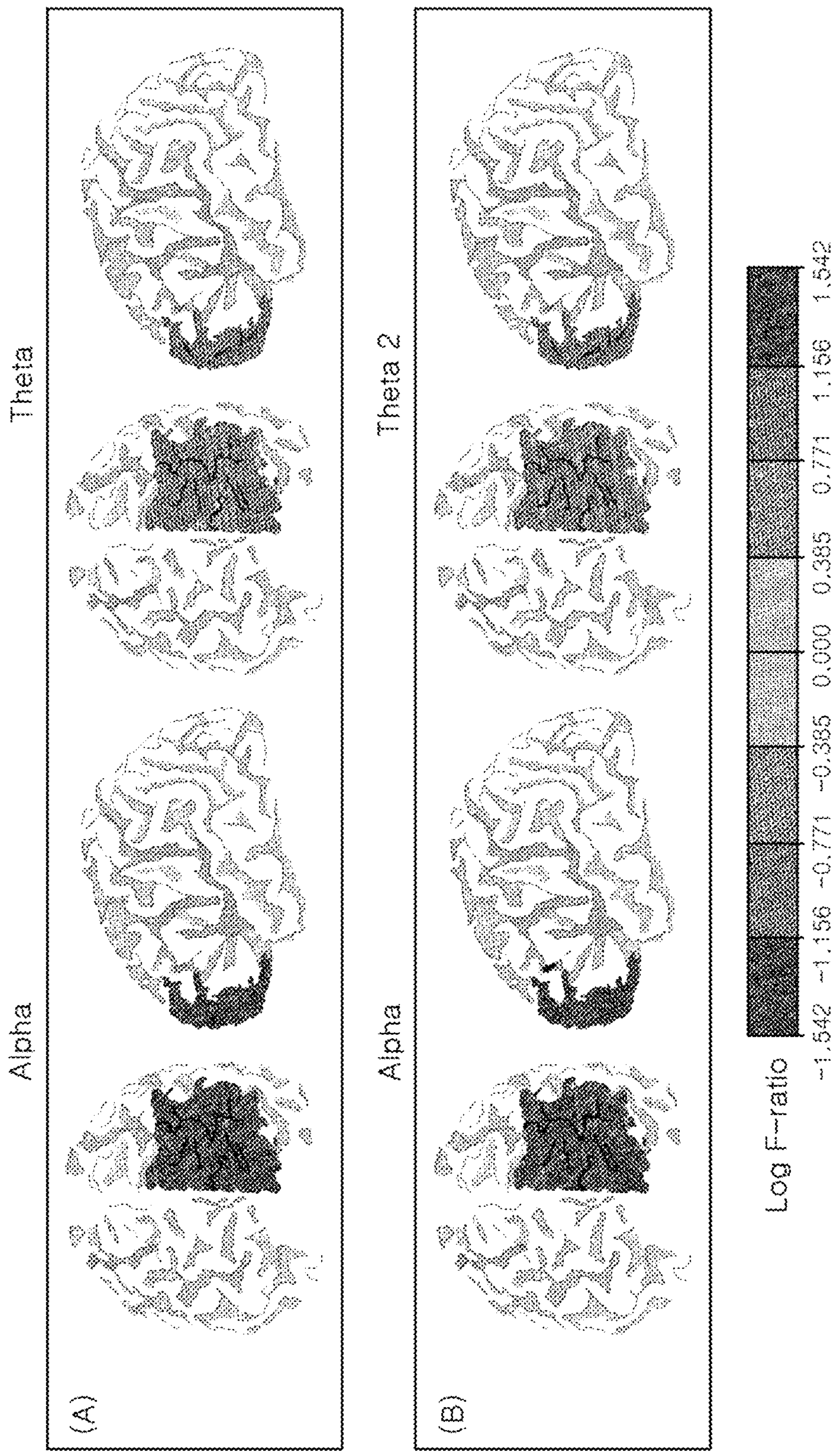
FIG. 13 is a diagram illustrating a power difference in cortical limited to a source of a prefrontal cortex according to one embodiment. In this case, power levels in alpha and theta frequency bands (see FIG. 13A) and theta and beta 2 frequency bands (see FIG. 13B) increased after the virtual reality (VR) tinnitus treatment.

Compared to the EEG data before the VR-based tinnitus intervention, the EEG data after the VR was analyzed based on the source location analysis results, and the ROI of the prefrontal cortex was compared accordingly. The significant differences were observed in the ROIs of the orbitofrontal cortex (OFC). As a result, the alpha (P=0.030) and theta (P=0.040) bands were found to significantly increase in all patients after the VR treatment program in the left orbitofrontal cortex (OFC, 10 L and 11 L) (see FIG. 13). Specifically, in the patient group with improved THI scores, the significant increase in theta (P=0.003) and high beta (P=0.005) was confirmed in the left OFC (10 L and 11 L).

In addition, the changes in each band were compared and assessed between the patient group with improved THI scores and the patient group with no improved THI scores. As a result, in the patient group (THI<Grade 2 and THI>Grade 3) separated based on THI score (THI<Grade 2 and THI>Grade 3), statistically significant differences were seen in theta (P=0.007) and high beta (P=0.001) bands in the left OFC (10 L and 11 L).

In addition, as a result of performing the non-parametric correlation analysis in all patient groups to see whether the change in the THI score was correlated with the change in myogenic activity of specific bands, in the left OFC (r=−0.627 and P=0.004), a significant negative correlation was confirmed between the change in the THI score and the increase in the high beta band. As a result of analyzing the theta band through the same process, it was confirmed that there was the significant correlation between the THI score and the ta band value in the left OFC (r=−0.490 and P=0.033). In the detailed analysis of the subscales of the THI, it was found that there is the significant correlation between the THI emotion score and the theta value of the left OFC (r=−0.494 and P=0.032).

In addition, for the patient group with the improved THI scores, alpha (P=0.028), lower beta (P=0.012) and gamma (P=0.015) bands in the left OFC area was significant after the treatment program. Similar changes were found in the right OFC area in the alpha (P=0.041) and theta (P=0.023) bands. In addition, in the subgroup with improved THI, the change in the left sgACC area was observed in the group of patients who performed the experiment. As a result of analysis in the patient group with improved THI, it showed that the theta (P=0.023) and gamma (P=0.028) bands tended to increase in this region accordingly.

Argument

This study assessed the value of VR-based psychological intervention as part of behavioral cognitive therapy for patients with tinnitus using a VR system with high visual, auditory, and tactile realism. This study started on the assumption that this method could be used for the recovery of patients with severe tinnitus. This analysis of the questionnaire showed that VR-based intervention alleviated the tinnitus and related symptoms. The THI and PSQI scores showed significant improvement, especially total score, grade, and functional status. The THI, which is useful for measuring the degree of tinnitus-related pain and predicting psychological distress, varies depending on the individual, but the scores improved in 12 out of 19 patients. PSQI, which indicates sleep quality, also decreased after the intervention, showing that the program helped alleviate the related symptoms such as insomnia caused by severe tinnitus. Meanwhile, the reason other questions did not show statistically significant differences is because indirect factors related to tinnitus are being assessed, and the change may be small due to the short treatment period.

This VR system was found to have relatively low motion sickness as a result of SSQ analysis. In a previous study, the SSQ score of the VR treatment system for chronic pain patients was 55.7226, and the SSQ score of the VR wheelchair training simulator system was 20027 or higher. On the other hand, the SSQ score of this VR system was 32.81. The lower SSQ scores indicate less motion sickness. The low SSQ score of the VR system indicates that the system itself did not cause the motion sickness problems. In addition, the EEG data before and after the experiment were carefully analyzed. The analysis confirmed that the myogenic activity in the alpha and theta bands increased in the left orbitofrontal cortex in all patient groups after the VR treatment program.

In general, a limbic system is highly associated with acoustic functions such as tinnitus and phantom sounds. This is due to the interaction between the limbic system and the auditory system, which may be related to the noise cancellation system. This system is closely related to the tinnitus-induced stress, which occurs due to the corresponding change in a prefrontal cortex system of the brain. Recently, in an integrative model of tinnitus that proposes tinnitus as an integrated perception in which separate subnetworks interact, the OFC has been proposed as the cortical area responsible for the emotional component of tinnitus. In particular, the area plays a role in directing attention and emotional regulation to suppress unwanted sensory signals while passing through thalamus and nucleus accumbens. In addition, mild structural and functional abnormalities of the PFC are often observed in patients with tinnitus. The recent study showed that the OFC has a positive correlation with percent improvement in numerical rating scale (NRS) pain in the OFC for the alpha frequency band and with the change in source regional cortical power in the OFC, which is related to excitatory activity rather than inhibitory activity related to feeling of pleasantness which is correlated with this cortical area. In addition, similar to these studies, as the EEG results, the connection between the alpha band of the OFC and the tinnitus was confirmed. As the EEG results of the patient after the tailored VR intervention, the increased myogenic activity in the alpha band indicating the increase in excitatory function suggests the restoration of the emotion regulation system related to the occurrence of tinnitus.

In this study, it was observed that the theta activity increased in the OFC. In the previous study, by the analysis of the source location of the theta change in the group with improved tinnitus through music therapy, it was found that the main causes of the change originated from the auditory processing area such as the superior temporal gyrus and the higher emotional and cognitive processing area such as the OFC. In addition, the abnormality and theta activity change in the limbic system area are frequently observed in patients with tinnitus, which is interpreted as a retrieval of auditory information from memory as compensation for insufficient sensory input to alleviate uncertainty which may lead to the accumulation of emotional memories associated with tinnitus. In addition, according to the previous research results, the OFC, which also plays a role in controlling to start working and working memory functions, is connected to the limbic system which may be expressed as the increased theta activity. Therefore, the results of patients with tinnitus who participated in this study may be evidence for improved cognitive control, especially inhibitory executive control in multisensory tasks and memory processes. This may occur due to the phase-locked theta activity correlated with this area in the improvement of top-down task performance and cognitive control in patients with tinnitus due to the symptom relief by this VR program.

In this study, additional analysis was performed on the group of patients with improved THI scores and the significant increases in the theta and high beta was confirmed in the left OFC. In addition, as a result of the comparative assessment, the statistically significant differences were found in the theta and high beta bands of the left OFC.

The beta band plays a similar role to the alpha band in the OFC area which is related to the emotional system. As suggested above, the beta band is closely related to the unpleasant emotion of tinnitus. As such, the beta band is a representation of change in pain detected by a network including the limbic system, which activates the anterior cingulate, amygdala, and insula for the prefrontal cortex system. As in the present results, the increase in the beta band may activate functional connections between the precuneus and OFC and dorsolateral prefrontal cortex (DLPFC), which are related to the emotional processing and, in turn, are closely related to the tinnitus relief system. This may direct attention and emotional regulation to suppress and alleviate stimulation caused by tinnitus.

In addition, in the patient group with improved THI scores, the alpha, low beta, and gamma bands in the left OFC area were not significant, but tended to increase after the treatment program. Therefore, these results suggest that additional factors were discovered through more detailed analysis as described above, and suggest consistency in the results due to the increase in the alpha band of the left OFC area that may be seen in all patient groups. The similar changes were found in the right OFC area in the alpha and theta bands. The change in the patient group participating in the experiment was observed in the leftsgACC area of the subgroup with reduced THI. The sgACC area closely regulates positive emotions, arousal processing networks, and error detection functions, and is also involved in tinnitus and side effects resulting from similar disorders such as chronic pain and post-traumatic stress disorder. According to another study, the higher activity in the ACC predicted a higher level of tinnitus pain felt by patients. The analysis of the group of patients with improved THI showed a trend to increase the theta and gamma bands in the area, which may be related to the restoration of the processing system.

In addition, through the non-parametric correlation analysis in all the patient groups, it was confirmed that the change in THI score after experiencing the VR treatment program was correlated with the change in source activity of a specific band, and it was confirmed that there was a significant negative correlation between the change in the THI score and the increase in the high beta band of the OFC ($r=-0.627$). That is, increasing high beta band values improved the THI scores in patients. In addition, as a result of analyzing the theta band through the same process, it was confirmed that there was a significant correlation between the THI score and the theta band value ($r=-0.490$) in the OFC. These results showed that the VR intervention program performed through this experiment is effective in clinically improving the tinnitus-related pain through the correlation with THI scores, and this is verified by the change in brain signals through the EEG. This study provides an understanding of the intervention-related change that appears to include the cortical area related to the central expression of the tinnitus-related pain.

In this study, the functional difference in the brain cortex related to the tinnitus after exposure to the VR program was assessed and it was confirmed that this program induced the brain-level change, especially in the OFC and sgACC areas. The change may lead to the remodulation of the perturbed network in the relevant region and may affect the modulation of the perturbed pathway. In this study, the VR program allowed participants to visualize the auditory stimuli, which led to the change in the OFC and sgACC mechanisms that process and regulate the tinnitus, thereby reducing the tinnitus. In other words, the roles of these areas related to cognition, mood, and affection are closely related to examples of the tinnitus and its effects, which may provide clues to the basic pathophysiology of tinnitus. Moreover, the band difference appearing in the EEG indicates the complementary network activation of these functions. Therefore, the cognitive behavioral therapy may induce the change in the occurrence of tinnitus and the persistent experience of tinnitus.

CONCLUSION

The chronic subjective tinnitus has several adverse effects on the lives of patients, and to date, there is no truly successful treatment method. Among the available treatment methods, the cognitive behavioral therapy has recently been in the spotlight. However, there are limitations that require a lot of attention and compliance from patients. Therefore, this study is to assess the potential of the VR intervention system to provide users with real experiences that may become part of the cognitive behavioral therapy treatment. In this study, the relief of the tinnitus symptoms and the change in the EEG pattern related to the tinnitus generating system were detected, and it is expected that new method of treating patients with tinnitus may be found.

The surround sound virtual reality interface for tinnitus treatment and symptom relief according to the above-described embodiment can be applied to a rehabilitation device for tinnitus and can be applied using a computer. The surround sound virtual reality interface may be applied to various fields such as symptom relief and treatment for tinnitus.

In this way, according to an embodiment, it is possible to provide an interface that may obtain positional information about tinnitus that exists in the virtual reality and sounds in the virtual environment. It is possible to simulate everyday situations where immersive tinnitus is heard through the sounds of the virtual tinnitus objects and the virtual environment objects. Going beyond the conventional treatment method of simply hearing the tinnitus sound, it allows the user to experience hearing the tinnitus sound in the virtual everyday space. By going beyond the stimulation of existing cognitive behavioral therapy and making the stimulation heard in a realistic environment, it is possible to provide a simulation environment that can more effectively reduce tinnitus stress in the everyday environment.

Figure 14:
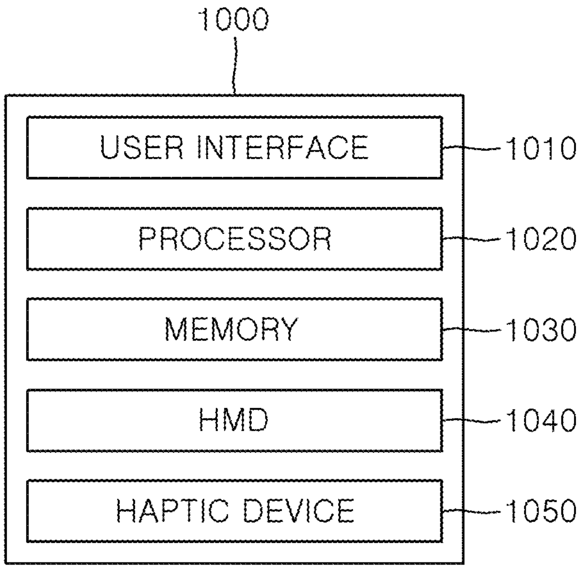
FIG. 14 is a diagram illustrating an example of hardware implementation of the tinnitus treatment device according to an embodiment.

FIG. 14 illustrates an example of hardware implementation of the tinnitus treatment device according to an embodiment. A tinnitus treatment device 1000 according to an embodiment may include a user interface 1010, a processor 1020, a memory 1030, an HMD 1040, and a haptic device 1050.

The user interface 1010 may acquire subjective tinnitus information from a user. The subjective tinnitus information may include a type of noise heard by the user, whether tinnitus occurs in left or right ears, frequency of occurrence, a size of tinnitus, etc. The user interface 1010 may include a keyboard, a joystick, a touch panel, etc., to acquire the subjective tinnitus information.

The processor 1020 may visualize subjective tinnitus perceived by a user from subjective tinnitus information using a subjective tinnitus visualization model stored in the memory 1030 to generate a virtual tinnitus object, and use the VR environment model stored in the memory 1030 to generate a virtual environment object corresponding to a sound source occurring in a virtual environment. In addition, the processor 1020 may perform 3D sound processing to allow the user to perceive the location of the virtual tinnitus object and the location of the virtual environment object. In addition, the processor 1020 may control the virtual tinnitus object displayed in the VR video in response to the user input signal input by the haptic device 1050, and change the output of the 3D sound in response to the control of the virtual tinnitus object. However, the operation of the processor 1020 is not limited thereto, and the operations described in FIGS. 1 to 13 may also be performed.

The memory 1030 may store the subjective tinnitus visualization model and the VR environment model. The subjective tinnitus visualization model may be composed of an algorithm that generates the virtual tinnitus object from the subjective tinnitus information. The VR environment model may be composed of an algorithm that generates the virtual environment object that exists in a specific virtual environment (a bedroom, a living room, a restaurant, a city street, etc.). The memory 1030 may temporarily or permanently store data required for performing a tinnitus processing method according to an embodiment. For example, the memory 1030 may store the subjective tinnitus information, the virtual tinnitus objects, the virtual environment objects, the user input signals, etc.

The HMD 1040 may display the VR video, into which the virtual tinnitus objects and the virtual environment objects are inserted, to the subject and output the 3D sound. The HMD 1040 may display the virtual tinnitus objects controlled in response to the user input signal and output the 3D sound changed accordingly.

The haptic device 1050 may receive the user input signal to change the content in the VR video and transfer the corresponding tactile sensation to the user according to the change in the content in the VR video.

The device 1000 according to the embodiment may generate the customized tinnitus avatar for the tinnitus patient and provide the generated customized tinnitus avatar to the virtual environment, and allows the tinnitus avatar to be controlled within the VR video through the user's active participation. In addition, this makes the tinnitus treatment possible through the hyper-reality (multisensory sensation) to which the user's active tactile function is added.

The interface according to the embodiment may be various types of electronic devices. The electronic devices may include, for example, portable communication devices (e.g., smartphones), computer devices, portable multimedia devices, portable medical devices, cameras, wearable devices, or home appliances. The electronic devices according to the embodiments of this document are not limited to the above-described devices.

Various embodiments of the present invention may be implemented as software (e.g., program) including one or more instructions stored in a storage medium (e.g., internal memory or external memory) that may be read by a machine (e.g., an electronic device). For example, a processor of a device (e.g., electronic device) may call at least one of one or more instructions stored from the storage medium and execute the called instruction. This makes it possible for the machine to be operated to perform at least one function according to the at least one instruction called. The one or more instructions may include codes generated by a compiler or codes executable by an interpreter. The machine-readable storage medium may be provided in a form of a non-transitory storage medium. Here, the 'non-transitory' means that the storage medium is a tangible device, and does not include a signal (for example, electromagnetic waves), and the term does not distinguish between the case where data is stored semi-permanently on a storage medium and the case where data is temporarily stored thereon.

According to an embodiment, the methods according to the diverse embodiments disclosed in the present invention may be included and provided in a computer program product. The computer program product may be traded as a product between a seller and a purchaser. The computer program product may be distributed in the form of a machine-readable storage medium (for example, compact disc read only memory (CD-ROM)), or may be distributed (for example, download or upload) through an application store (for example, Play Store™) or may be directly distributed (for example, download or upload) between two user devices (for example, smart phones) online. In case of the online distribution, at least a portion of the computer program product may be at least temporarily stored in a storage medium readable by a device such as a memory of a server of a manufacturer, a server of an application store, or a relay server or be temporarily generated.

According to various embodiments, each component (for example, module or program) of the above-described components may include one entity or a plurality of entities. According to various embodiments, one or more components or operations among the above-described corresponding components may be omitted, or one or more other components or operations may be added. Alternatively or additionally, a plurality of components (for example, module or program) may be integrated into a single component. In this case, the integrated component may perform one or more functions of each component of the plurality of components in the same as or similar to that performed by the corresponding component among the plurality of components prior to the integration. According to various embodiments, operations performed by a module, a program, or other components may be executed sequentially, in parallel, repeatedly, or heuristically, or one or more of the operations may be executed in a different order or omitted, or one or more other operations may be added.

The present technology can induce a user's active participation and control both a visual cognitive function and an auditory cognitive function, thereby obtaining tinnitus symptom relief and treatment effects.

In addition, the present technology can increase tinnitus treatment efficiency by the tinnitus treatment through hyper-reality (multisensory sensation) in which a tactile function is added to the visual and auditory function.

Although the spirit and scope of the present invention have been described in detail according to exemplary embodiments, it is to be noted that the exemplary embodiments are provided in order to describe the present invention rather than limiting the present invention. Further, it may be understood by those skilled in the art to which the present invention pertains that various exemplary embodiments are possible without departing from the spirit and scope of the present invention.

What is claimed is:

1. A tinnitus treatment device using a surround sound virtual reality (VR) interface, comprising:

a display unit provided as a head mounted display to display a VR video, into which a virtual tinnitus object and a virtual environment object are inserted, to a subject;

a virtual tinnitus object and virtual environment object unit that visualizes subjective tinnitus perceived by a user to generate the virtual tinnitus object and generate the virtual environment object corresponding to a sound source occurring in a virtual environment;

a surround sound processing unit that performs three-dimensional (3D) sound processing to allow the user to perceive a location of the virtual tinnitus object and a location of the virtual environment object;

a sound output unit that outputs a 3D sound to the user; and a VR video control unit that changes content in the VR video in response to a user input signal provided from a user interface, wherein the VR video control unit controls the virtual tinnitus object displayed in the VR video in response to the user input signal and changes the output of the 3D sound in response to the control of the virtual tinnitus object, and wherein the VR video control unit removes the virtual tinnitus object displayed in the VR video in response to the user input signal, and at the same time maintains the output of the 3D sound due to the virtual environment object while stopping the output of the 3D sound due to the virtual tinnitus object.

2. The tinnitus treatment device of claim 1, wherein the VR video control unit gradually removes the virtual tinnitus object displayed in the VR video in response to the user input signal, and at the same time gradually reduces the output of the 3D sound due to the virtual tinnitus object.

3. The tinnitus treatment device of claim 1, wherein the 3D sound is a mixed sound in which the 3D sound due to the virtual tinnitus object and the 3D sound due to the virtual environment object are mixed.

4. The tinnitus treatment device of claim 1, wherein the sound output unit includes a left sound output unit and a right sound output unit that output sound to both ears of the user.

5. The tinnitus treatment device of claim 1, wherein the surround sound processing unit adjusts a time, loudness, and a pitch of the 3D sound depending on a distance between the user and the virtual tinnitus object and a distance between the user and the virtual environment object within the VR video.

6. The tinnitus treatment device of claim 5, wherein the surround sound processing unit is implemented based on a head-related transfer function (HRTF), which is a function that sets a time, loudness, and a pitch of the 3D sound according to movement of the head mounted display.

7. The tinnitus treatment device of claim 1, wherein the head mounted display provides a closed viewing environment blocked from an outside.

8. A tinnitus treatment system using a surround sound virtual reality (VR) interface, comprising:

a tinnitus treatment device; and a VR video controller that is connected to the tinnitus treatment device through a network and inputs a user input signal to the tinnitus treatment device, wherein the tinnitus treatment device includes:

a display unit provided as a head mounted display to display a VR video, into which a virtual tinnitus object and a virtual environment object are inserted, to a subject;

a virtual tinnitus object and virtual environment object unit that visualizes subjective tinnitus perceived by a user to generate the virtual tinnitus object and generate a virtual environment object corresponding to a sound source occurring in the virtual environment;

a surround sound processing unit that performs three-dimensional (3D) sound processing to allow the user to perceive a location of the virtual tinnitus object and a location of the virtual environment object;

a sound output unit that outputs a 3D sound to the user; and a VR video control unit that changes content in the VR video in response to a user input signal provided from the VR video controller, and the VR video control unit controls the virtual tinnitus object displayed in the VR video in response to the user input signal and changes the output of the 3D sound in response to the control of the virtual tinnitus object, and wherein the VR video control unit removes the virtual tinnitus object displayed in the VR video in response to the user input signal, and at the same time maintains the output of the 3D sound due to the virtual environment object while stopping the output of the 3D sound due to the virtual tinnitus object.

9. A tinnitus treatment device using a surround sound virtual reality (VR) interface, comprising:

a user interface that acquires subjective tinnitus information from a user;

a processor that visualizes subjective tinnitus perceived by the user from the acquired subjective tinnitus information to generate a virtual tinnitus object and generate a virtual environment object corresponding to a sound source occurring in a virtual environment, and performs 3D sound processing to allow the user to perceive a location of the virtual tinnitus object and a location of the virtual environment object;

a head mounted display (HMD) that displays a VR video into which the virtual tinnitus object and the virtual environment object are inserted and outputs a 3D sound to a subject; and a haptic device that receives a user input signal for changing content in the VR video and transfers a corresponding tactile sensation to the user according to a change in the content in the VR video, wherein the processor controls the virtual tinnitus object displayed in the VR video in response to the user input signal and changes the output of the 3D sound in response to the control of the virtual tinnitus object, and wherein the processor removes the virtual tinnitus object displayed in the VR video in response to the user input signal, and at the same time maintains the output of the 3D sound due to the virtual environment object while stopping the output of the 3D sound due to the virtual tinnitus object.

10. The tinnitus treatment device of claim 9, wherein the processor gradually removes the virtual tinnitus object displayed in the VR video in response to the user input signal, and at the same time gradually reduces the output of the 3D sound due to the virtual tinnitus object.

11. The tinnitus treatment device of claim 9, wherein the processor gradually removes a size of the virtual tinnitus object displayed in the VR video in response to the user input signal, and at the same time gradually reduces the output of the 3D sound due to the virtual tinnitus object.

12. The tinnitus treatment device of claim 11, wherein a level at which the size of the virtual tinnitus object is gradually reduced and a level at which the output of the 3D sound due to the virtual tinnitus object is gradually reduced correspond to each other.

13. The tinnitus treatment device of claim 9, wherein the haptic device generates the corresponding tactile sensation when a size of the virtual tinnitus object is gradually reduced and transfers the generated tactile sensation to the user.

14. The tinnitus treatment device of claim 9, wherein the haptic device is a phantom haptic device.

* * * * *